United States Patent
Matsumoto et al.

(10) Patent No.: US 7,411,675 B2
(45) Date of Patent: Aug. 12, 2008

(54) OPTICAL ROTATION ANGLE MEASURING APPARATUS

(75) Inventors: Kenji Matsumoto, Tokyo (JP); Takakazu Yano, Tokyo (JP); Tadahiro Fukuda, Tokyo (JP); Shigeru Futakami, Tokorozawa (JP)

(73) Assignee: Citizen Holdings Co., Ltd., Tokyo (JP)

( * ) Notice: Subject to any disclaimer, the term of this patent is extended or adjusted under 35 U.S.C. 154(b) by 406 days.

(21) Appl. No.: 10/551,796

(22) PCT Filed: Mar. 26, 2004

(86) PCT No.: PCT/JP2004/004261

§ 371 (c)(1),
(2), (4) Date: Sep. 28, 2005

(87) PCT Pub. No.: WO2004/088286

PCT Pub. Date: Oct. 14, 2004

(65) Prior Publication Data

US 2006/0087653 A1    Apr. 27, 2006

(30) Foreign Application Priority Data

Mar. 28, 2003  (JP) .............................. 2003-089592
Oct. 10, 2003  (JP) .............................. 2003-351725

(51) Int. Cl.
*G01J 4/00*     (2006.01)
*G02F 1/01*     (2006.01)

(52) U.S. Cl. ...................................... 356/364; 250/225

(58) Field of Classification Search ......... 356/356–370, 356/39; 250/225; 600/316, 322
See application file for complete search history.

(56) References Cited

U.S. PATENT DOCUMENTS

| 5,009,230 | A  |   | 4/1991  | Hutchinson |
| 5,448,992 | A  | * | 9/1995  | Kupershmidt ............... 600/347 |
| 6,175,412 | B1 |   | 1/2001  | Drevillon et al. |
| 6,620,622 | B1 | * | 9/2003  | Kawamura .................. 436/164 |
| 6,804,002 | B2 | * | 10/2004 | Fine et al. .................. 356/364 |
| 6,885,882 | B2 | * | 4/2005  | Cote et al. .................. 600/319 |

(Continued)

FOREIGN PATENT DOCUMENTS

EP    0591903 A1    4/1994

(Continued)

*Primary Examiner*—L. G Lauchman
(74) *Attorney, Agent, or Firm*—Sughrue Mion, PLLC

(57) ABSTRACT

A linearly polarized light output unit (701) outputs a linearly polarized light. A first phase modulation unit (703) includes a first polarization axis and modulates a phase of the linearly polarized light. A second phase modulation unit (704) includes a second polarization axis orthogonal to the first polarization axis and modulates the phase of the linearly polarized light. A signal supply unit (705) supplies a modulation signal (vb) for modulating the phase of the linearly polarized light to one of the phase modulation units. A light intensity detection unit (707) detects an intensity of a light emitted from a phase modulation unit (702), to which the signal is supplied, to a sample (106) that contains an optically active material by causing a polarization plane of the light to be rotated and the light to be transmitted by the sample (106). An optical rotation angle calculation unit (708) calculates an optical rotation angle based on the modulation signal (Vb) and the detected light intensity.

20 Claims, 15 Drawing Sheets

U.S. PATENT DOCUMENTS 7,084,976 B2 * 8/2006 Morokawa et al. .......... 356/364
7,248,905 B2 * 7/2007 Fukuda et al. .............. 600/310

FOREIGN PATENT DOCUMENTS

| EP | 1387161 A | 2/2004 |
| FR | 2 755 254 A1 | 4/1998 |
| JP | 4-355715 A | 12/1992 |
| JP | 6-118359 A | 4/1994 |
| JP | 7-218889 A | 8/1995 |
| JP | 9-145605 A | 6/1997 |
| JP | 2000-502461 A | 2/2000 |
| JP | 2001-356089 A | 12/2001 |
| JP | 2002-277387 A | 9/2002 |
| JP | 2004-69452 A | 3/2004 |

* cited by examiner

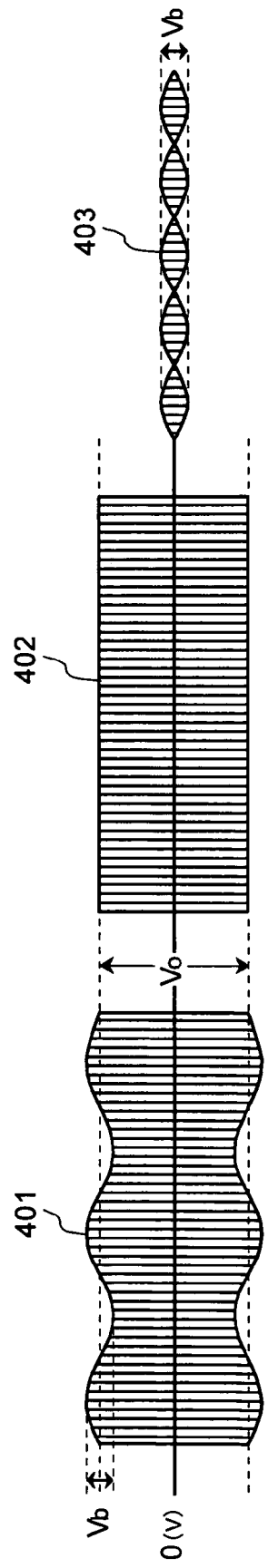

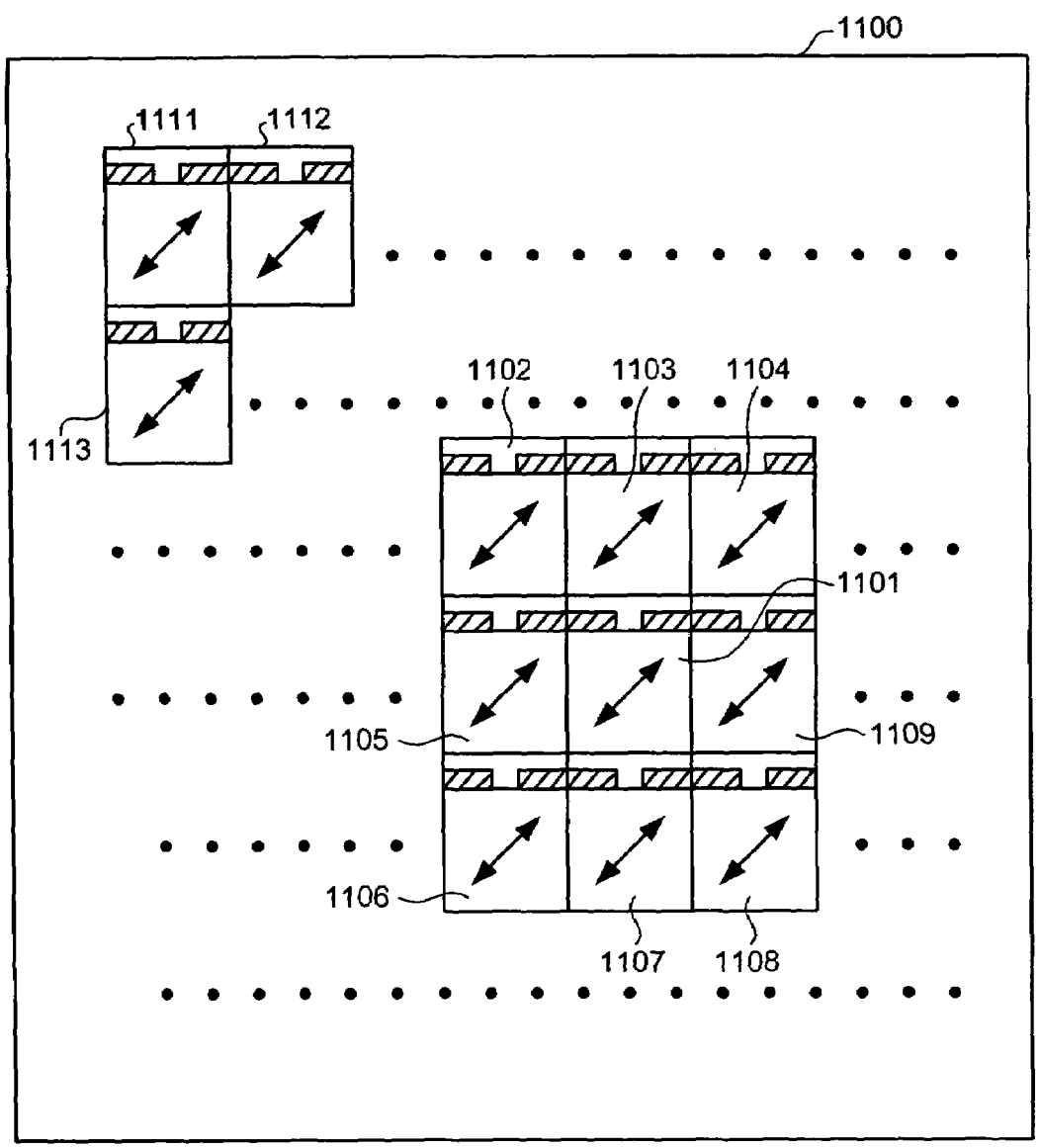

OPTICAL ROTATION ANGLE MEASURING APPARATUS

TECHNICAL FIELD

The present invention relates to an optical rotation angle measuring apparatus that measures an optical rotation angle of a sample.

BACKGROUND ART

Conventionally, an angle of rotation of a polarization plane rotated by a sample, that is, an optical rotation angle (also referred to as "an optical rotary power") is calculated from a signal obtained by causing a linearly polarized light to be incident on the sample, causing a light-flux transmitted by the sample to be incident on an analyzer, and photoelectrically converting the light-flux into an electric signal using a photodiode.

Assuming that a gradient of a transmission axis of the analyzer with respect to a transmission axis of a polarizer is $\theta$ and that an optical rotation angle by the sample is $\alpha$, an intensity I of the light received by the photodiode is represented by the following Equation (1): $I = T \times I_0 \cos(\theta - \alpha)^2$. In the Equation (1), symbol T denotes transmissivity in consideration of all attenuations caused by reflections and absorptions of the sample, the polarizer, and the analyzer, and symbol $I_0$ denotes an intensity of the incident light.

As evident from the Equation (1), a minimum point is obtained per rotation angle $\pi$ (rad) following rotation of the analyzer. The optical rotation angle can be calculated from the angle of the analyzer at this minimum point.

For purposes of improving accuracy and sensitivity, a method for vibrating the polarization plane is normally used, which method will be explained with reference to FIG. 18. FIG. 18 is an explanatory diagram of a conventional optical rotation angle measuring apparatus using a method for vibrating the polarization plane. A monochrome light emitted from a light source 1821 is incident on a polarizer 1822 vibrated at a frequency f and an angular amplitude $\theta$ by a polarizer driver circuit 1829. The incident light is thereby transformed into a linearly polarized light having a rotated and vibrated polarization plane.

If a light-flux of this linearly polarized light is made incident on a sample 1825 and transmitted by an analyzer 1823, a signal at the frequency f is obtained from a photodiode 1824. If the polarization plane is rotated by $\alpha$ by the optical rotary power of the sample 1825, the signal having a phase inverted according to whether the sample 1825 rotates clockwise or counterclockwise can be obtained by arranging the polarizer 1822 and the analyzer 1823 orthogonal to each other.

The signal obtained from the photodiode 1824 is amplified by an amplifier circuit 1826, and synchronized and rectified by a rectifying and filtering circuit 1827, thereby calculating the phase of the signal. According to the phase, the analyzer 1823 is rotated forward or backward through an analyzer driver circuit 1828. As a consequence, the angle of the analyzer is determined by optical null method so that a quantity of transmitted light is a minimum. The angle of the analyzer at this equilibrium point corresponds to the optical rotation angle by the sample 1825.

Alternatively, if the phase of the signal obtained from the photodiode 1824 is detected at the modulation frequency f, a signal component at the frequency f is extracted, and the angle of the analyzer is adjusted so that an intensity of this signal is a minimum, the same result can be obtained.

As the method for vibrating and rotating the polarization plane, a method using a Faraday rotor that utilizes Faraday effect is also known as well as the method for mechanically rotating the polarizer. For example, a method for measuring the optical rotation angle by applying a magnetic field and using the Faraday effect has been suggested (see, for example, patent document 1: Japanese Patent Application Laid-Open No. H9-145605 (FIG. 7)).

As a similar method for measuring the optical rotation angle, a method using a liquid crystal element as a modulation element represented by the Faraday cell explained above has been suggested. This method has advantages of low power consumption driving, size reduction, and the like (see, for example, patent document 2: Japanese Patent Application Laid-Open No. 2002-277387 (FIG. 7)).

As for use of the liquid crystal element to rotate a linear light, there is known a Senarmont azimuth rotator configured by a combination of a liquid crystal element and a quarter-wave plate. As a development of this rotator, there is known an invention of a device that is configured so that three liquid crystal elements to which a variable voltage can be applied are arranged in series in a light irradiation direction and that enables optical modulation having higher flexibility (see, for example, patent document 3: Japanese Patent Application Laid-Open No. H7-218889 (FIG. 3)).

As a concentration measuring apparatus using an optical rotary power of a liquid crystal element, there is known an invention characterized by not including a conventional mechanical operating unit (see, for example, patent document 4: Japanese Patent Application Laid-Open No. 2001-356089 (FIG. 2)).

As a further development, there is known an invention that enables high accuracy, stable measurement by periodic phase modulation using a liquid crystal element (see, for example, patent document 5: Japanese Patent Application Laid-open No. 2002-277387 (FIG. 3)). FIG. 19 is an explanatory diagram of an optical system of the conventional concentration measuring apparatus.

A light-flux emitted from a laser diode 1921 is collimated into a parallel light by a lens 1922. This parallel light is polarized by a polarizer 1923A into an linearly polarized light vibrating in a direction inclined by 45 degrees with respect to a vertical direction.

Both of or one of polarized components of the light emitted from the polarizer 1923A in horizontal and vertical directions is subjected to phase modulation by a liquid crystal element 1931. The liquid crystal element 1931 is a homogeneous alignment-type liquid crystal element in which major axes of liquid crystal molecules are aligned in either the horizontal direction or the vertical direction. In this homogeneous alignment-type liquid crystal element 1931, the liquid crystal molecules stand upright when a voltage is applied thereto, and a refractive index in a molecular major axis direction is changed, whereby phase modulation can be performed. If the liquid crystal element 1931 modulates the phase of only one polarized component, linearly polarized lights interfere with each other.

The transmission light transmitted by the liquid crystal element 1931 is split into a reflective light and a rectilinear light by a half mirror 1924. The rectilinear light is incident on a quarter-wave plate 1926A with a horizontal axis and a vertical axis inclined by 45 degrees. As a result, vibrating components of the incident rectilinear light in the horizontal and vertical directions can be converted into circularly polarized components rotating in opposite directions.

The rectilinear light transmitted by the quarter-wave plate 1926A is made incident on a sample 1925, whereby a phase difference of ±θ is generated between a clockwise circularly polarized light and a counterclockwise circularly polarized light according to the optical rotation angle by the sample 1925. Namely, if the rectilinear light transmitted by the quarter-wave plate 1926A is incident on the sample 1925, the clockwise circularly polarized light and the counterclockwise circularly polarized light are emitted from the sample 1925 with the phase difference of ±θ therebetween.

On the other hand, the reflective light from the half mirror 1924 is incident on a polarizer 1923C. The light transmitted by the polarizer 1923C is incident on a photodiode 1929B, and converted into an electric signal by a photodiode 1929B, thereby generating a beat signal.

The clockwise circularly polarized light and the counterclockwise circularly polarized light emitted from the sample 1925 are transmitted by a quarter-wave plate 1926B having an optical axis equal to or orthogonal to that of the quarter-wave plate 1926A. The clockwise circularly polarized light and the counterclockwise circularly polarized light are thereby converted into polarized components orthogonal to the horizontal or vertical direction, respectively.

The transmission light transmitted by the quarter-wave plate 1926B is transmitted by a polarizer 1923B inclined by 45 degrees with respect to the horizontal or vertical direction. Interfering signals between the linearly polarized lights can be thereby obtained. Furthermore, since the light-flux of one of the linearly polarized lights is phase-modulated, a beat signal is obtained and converted into an electric signal by a photodiode 1929A. The beat signal obtained by the photodiode 1929B is not influenced by the optical rotation angle by the sample 1925, so that the optical rotation angle by the sample 1925 can be obtained based on the phase difference between the signals from the photodiodes 1929A and 1929B.

However, as explained, it is necessary to mechanically rotate the polarizers and perform azimuth rotation and modulation using the Faraday effect as represented by the Faraday rotor so as to realize an azimuth rotator necessary for the measurement. This disadvantageously makes the optical rotation angle measuring apparatus large in size and expensive.

Meanwhile, if the liquid crystal element is used, the optical rotation angle measuring apparatus can be made small in size and driven at low power consumption. However, the optical rotation angle measuring apparatus using the liquid crystal element is disadvantageous in large fluctuations due to external environment such as temperature or atmospheric pressure. As a result, it is necessary to additionally provide a device such as a temperature controller in the optical rotation angle measuring apparatus so as to improve stability of measurement results. Such an apparatus is similarly disadvantageously made large in size, and expensive.

Furthermore, if an optical measurement system using the liquid crystal element is to be specifically realized, it is important to determine what structure is to be adopted to hold the liquid crystal element as well as optical components. However, the conventional techniques do not at all disclose this respect, so that the conventional techniques have a disadvantage in that stable and precise measurement cannot be ensured.

The present invention has been achieved in view of the conventional disadvantages. It is an object of the present invention to provide an optical rotation angle measuring apparatus that can be made small in size and ensure high accuracy in measuring the optical rotation angle with a simple configuration.

DISCLOSURE OF INVENTION

To solve the above problems and to achieve the object, an optical rotation angle measuring apparatus according to the present invention includes: a linearly polarized light output section that outputs a linearly polarized light; a first phase modulation section, having a first polarization axis in a predetermined direction, that modulates a phase of the linearly polarized light output from the linearly polarized light output section; a second phase modulation section, having a second polarization axis orthogonal to the first polarization axis, that modulates the phase of the linearly polarized light output from the linearly polarized light output section; a signal supply section that supplies a modulation signal having a predetermined amplitude for modulating the phase of the linearly polarized light to one of the first and the second phase modulation section; a light intensity detection section that detects an intensity of a light emitted from the first and the second phase modulation section, to which the signal is supplied from the signal supply section, and transmitted by a sample containing an optically active material that rotates a polarization plane of the light; and an optical rotation angle calculation section that calculates an optical rotation angle by the sample based on the modulation signal supplied from the signal supply section and the intensity of the light detected by the light intensity detection section.

According to the present invention, when modulation characteristics of the first phase modulation section and the second phase modulation section are changed by an external temperature change, an atmospheric pressure change, or the like, fluctuations can be cancelled since the polarization axes of the both sections are orthogonal to each other.

Furthermore, in the above invention, the signal supply section supplies a preset offset signal to the first and the second phase modulation sections.

According to the present invention, operations of the first phase modulation section and the second phase modulation section can be stabilized. In addition, since the polarization axes of the first phase modulation section and the second phase modulation section are orthogonal to each other, a predetermined bias signal can be cancelled and only a desired phase modulation amount can be obtained.

Moreover, in the above invention, the first phase modulation section includes a first liquid crystal element a liquid crystal orientation direction of which is a direction of the first polarization axis, and the second phase modulation section includes a second liquid crystal element which is different from the first liquid crystal element and a liquid crystal orientation direction of which is a direction of the second polarization axis.

According to the present invention, the liquid crystal elements are adopted as the phase modulating section. Therefore, when the modulation characteristics of the first liquid crystal element and the second liquid crystal elements are changed by the external temperature change, the atmospheric pressure change or the like, the fluctuations in the elements can cancel each other since the orientation directions are orthogonal to each other. It is thereby possible to stably drive the liquid crystal elements and perform the phase modulation by as much as only the fluctuation in the difference between the signals supplied to the first liquid crystal element and the second liquid crystal element. In addition, since the fluctuations cancel each other, the modulation amount of the liquid crystal element is minimized, thereby making it possible to easily determine positions of optical axes of optical components other than the liquid crystal elements.

Moreover, in the above invention, the first and the second liquid crystal elements are liquid crystal elements manufactured at predetermined manufacturing steps, manufactured on an equal liquid crystal substrate, and equal in structure. It is desirable that the first liquid crystal element is a liquid crystal element manufactured in an arbitrary position on the liquid crystal substrate, and the second liquid crystal element is a liquid crystal element manufactured near the first liquid crystal element on the liquid crystal substrate.

According to the present invention, the first and the second liquid crystal elements are manufactured according to the same specifications. Therefore, when the modulation characteristics of the first and the second liquid crystal elements are changed by the external environmental change such as the temperature change, the fluctuations can cancel each other since the first and the second liquid crystal elements exhibit the same characteristic change and are orthogonal to each other.

Moreover, in the above invention, the first and the second liquid crystal elements are homogeneous alignment-type liquid crystal elements.

According to the present invention, by adopting the homogenous alignment-type liquid crystal elements, the orientation directions of the respective liquid crystal elements can be specified to one direction and the apparatus can be easily manufactured.

Moreover, in the above invention, the first and the second liquid crystal elements include electrode substrates and counter substrates between which liquid crystals are held, respectively, and are equal in the liquid crystal orientation direction and equal in structure, and the first and the second liquid crystal elements are arranged in series to an optical path from the linearly polarized light output section to the light intensity detection section so that the liquid crystal orientation direction of the first liquid crystal element is orthogonal to the liquid crystal orientation direction of the second liquid crystal element.

According to the present invention, the first and the second liquid crystal elements have the same structure. Therefore, when the modulation characteristics of the first and the second liquid crystal elements are changed by the external environmental change such as the temperature change, the fluctuations can cancel each other since the first and the second liquid crystal elements exhibit the same characteristic change and are orthogonal to each other.

Moreover, in the above invention, the first and the second liquid crystal elements are arranged so that the electrode substrates or the counter substrates of the respective liquid crystal elements face each other.

According to the present invention, wirings can be easily connected to the signal supply section. Particularly if the liquid crystal orientation directions of the first and the second liquid crystal elements are inclined by 45 degrees with respect to the vertical axis, the liquid crystal orientation directions of the first and the second liquid crystal elements can be made orthogonal to each other by arranging the first and the second liquid crystal elements so that the electrode substrates or counter substrates thereof face each other.

Moreover, in the above invention, at least one of the first and the second liquid crystal elements includes: a rectangular first substrate including a first electrode; a rectangular second substrate including a second electrode, the liquid crystal held between the first electrode and the second electrode; a first input electrode for inputting the signal from the signal supply section to the first electrode; and a second input electrode for inputting the signal from the signal supply section to the second electrode. The first and the second input electrodes are provided near one end side of the second substrate along the end side, and the first and the second input electrodes are also provided near an end side other than the one end side of the second substrate.

Specifically, the first liquid crystal element includes: a rectangular first substrate including a first electrode; a rectangular second substrate including a second electrode, the liquid crystal being held between the first electrode and the second electrode, the second substrate being larger than the first substrate; a first input electrode for inputting the signal from the signal supply section to the first electrode; and a second input electrode for inputting the signal from the signal supply section to the second electrode. The first and the second input electrodes are arranged in series near one end side of the second substrate along the end side. The first and the second input electrodes are arranged in series near an end side orthogonal to the one end side of the second substrate. The second liquid crystal is equal to the first liquid crystal in the liquid crystal orientation direction and in structure. The first and the second liquid crystal elements are arranged in series on an optical path from the linearly polarized light output section to the light intensity detection section so that the liquid crystal orientation direction of the first liquid crystal element is orthogonal to the liquid crystal orientation direction of the second liquid crystal element.

According to the present invention, it is possible to share the wiring lead-out direction between the first and the second liquid crystal elements with respect to the signal supply section.

Moreover, the above invention further includes a liquid crystal element holding section that holds the first and the second liquid crystal elements.

According to the present invention, the first and the second liquid crystal elements can be held under the same conditions.

Moreover, the above invention further includes a pair of quarter-wave plates arranged in series on an optical path from the linearly polarized light output section to the light intensity detection section while the sample is held between the pair of quarter-wave plates.

According to the present invention, the quarter-wave plate on the linearly polarized light output section side transforms the light from the first and the second phase modulation section into the linearly polarized light and the light can be made incident on the sample. In addition, an error generated by this quarter-wave plate can be cancelled by the quarter-wave plate on the light intensity detection section side.

Moreover, in the above invention, the first phase modulation section is a first pixel group constituted by a part of a plurality of pixels that constitute a single liquid crystal element, and the second phase modulation section is a second pixel group constituted by pixels other than the part of the plurality of pixels that constitute the single liquid crystal element, the other pixels and the part of pixels being alternately arranged.

According to the present invention, the same advantages as those when the two liquid crystal elements are arranged in series can be attained. In addition, the first and the second phase modulation section can be constituted by a single liquid crystal element, a space within the apparatus can be saved and the number of components can be reduced.

Moreover, the above invention further includes a condensing section, provided between the first and the second pixel groups and the light intensity detection section, for condensing the light emitted from the first and the second pixel groups and transmitted by the sample containing the optically active material that rotates the polarization plane of the light, and for emitting the light to the light intensity detection section.

According to the present invention, even if the number of pixels is very small, the same advantages as those when the two liquid crystal elements are arranged in series can be attained. In addition, a single liquid crystal element having a small number of pixels can be adopted, whereby the liquid crystal element can be provided at low cost.

Moreover, in the above invention, the offset signal supplied from the signal supply section is a signal in a section in which a phase modulation amount of the liquid crystal element is linearly changed.

According to the present invention, the signal in the section in which the phase modulation amount of the liquid crystal element is linearly changed is used. The fluctuation in the difference between the signal supplied to the liquid crystal element and that supplied to the second liquid crystal element can be a fluctuation in a very narrow range. It is, therefore, possible to narrow the range of this fluctuation and improve phase modulation sensitivity.

BRIEF DESCRIPTION OF DRAWINGS

FIG. 4 is an explanatory diagram of a case that a driving voltage is applied to two liquid crystal elements, liquid crystal orientation directions of which are orthogonal to each other;

FIG. 11 is a plan view of a liquid crystal substrate on which the liquid crystal element employed in the optical rotation angle measuring apparatus is manufactured;

BEST MODE(S) FOR CARRYING OUT THE INVENTION

Exemplary embodiments of the present invention will be explained in detail with reference to the accompanying drawings.

First Embodiment (Hardware Configuration of Optical Rotation Angle Measuring Apparatus)

Figure 1:
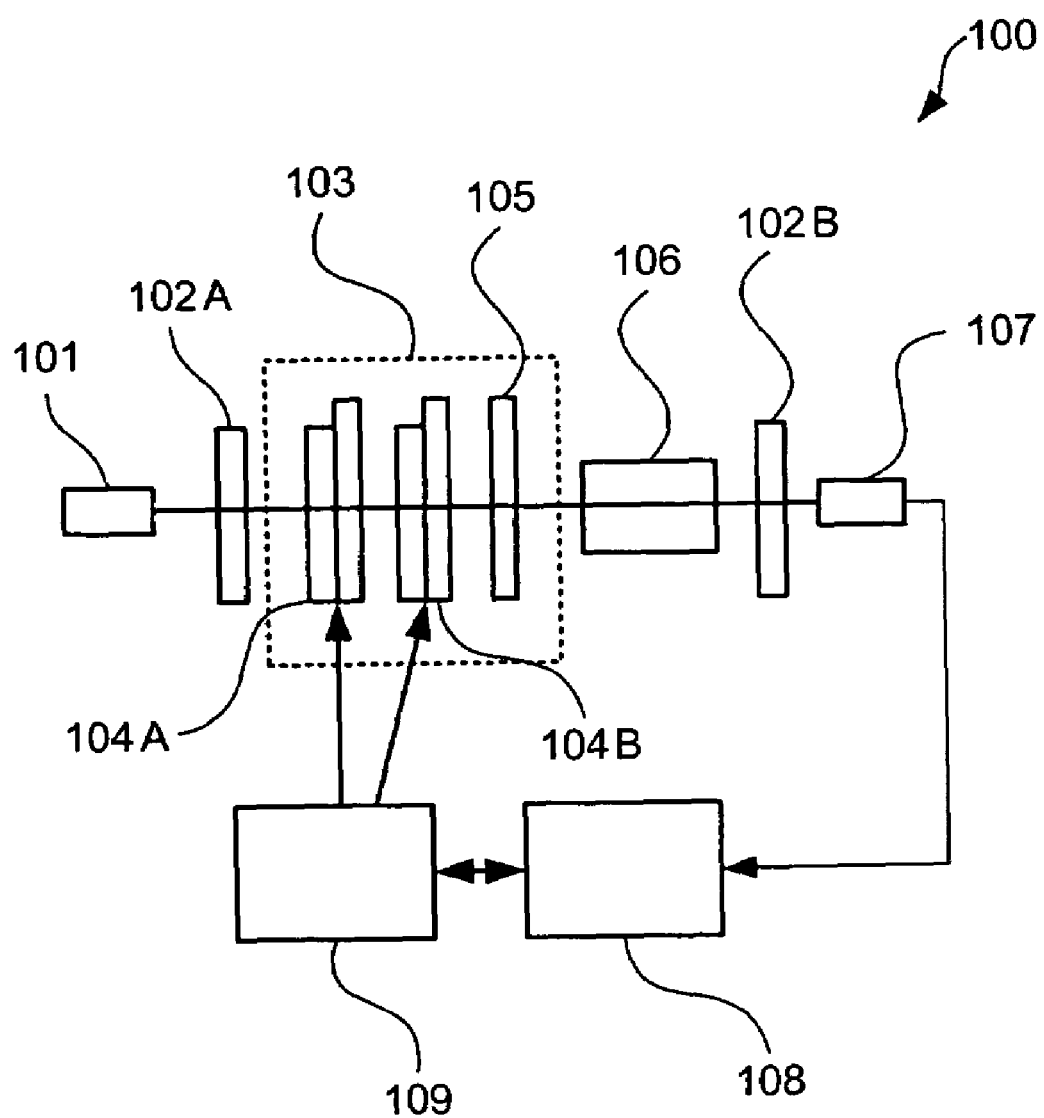
FIG. 1 is a block diagram of a hardware configuration of an optical rotation angle measuring apparatus according to a first embodiment of the present invention.

A hardware configuration of an optical rotation angle measuring apparatus according to a first embodiment of the present invention will be explained. FIG. 1 is a block diagram of the hardware configuration of the optical rotation angle measuring apparatus according to the first embodiment of the present invention. An optical rotation angle measuring apparatus 100 includes a light source 101, a polarizer 102A, an azimuth rotator 103, a polarizer 102B, a photodiode 107, an arithmetic processor 108, and a liquid crystal driver 109.

The light source 101 includes, for example, a laser diode, a driver circuit, an oscillator circuit, and a DC power supply. The driver circuit drives the laser diode to have a single intensity and a single frequency. The oscillator circuit outputs a clock signal to the driver circuit. The light source 101 thereby receives a power from the DC power supply and irradiates a laser light at a predetermined wavelength onto the polarizer 102A.

The polarizer 102A includes a polarization axis in a Y-axis direction that represents a vertical direction. The polarizer 102A transforms the laser light irradiated from the light source 101 into a linearly polarized light. The polarizer 102A emits the linearly polarized light to the azimuth rotator 103.

The azimuth rotator 103, which includes liquid crystal elements 104A and 104B and a quarter-wave plate 105, modulates the linearly polarized light transmitted by the polarizer 102A. Specifically, the liquid crystal elements 104A and 104B transform the incident linearly polarized light into an elliptically polarized light. The quarter-wave plate 105 transforms the elliptically polarized light obtained by the liquid crystal elements 104A and 104B into an linearly polarized light. The azimuth rotator 103 emits this linearly polarized light to a sample 106.

The polarizer 102B includes a second polarization axis in an X-axis direction that represents a horizontal direction. Namely, the polarization axis of the polarizer 102A is orthogonal to that of the polarizer 102B. The light transmitted by the sample 106 is incident on the polarizer 102B. The light transmitted by the polarizer 102B is emitted to the photodiode 107.

The photodiode 107 photoelectrically converts the incident light into an electric signal. The photodiode 107 outputs the electric signal obtained by this photoelectric conversion to the arithmetic processor 108.

The arithmetic processor 108 executes processing such as an input processing for supply of the DC power to the laser diode included in the light source 101, an input processing for driving of the liquid crystal driver 109, an arithmetic processing for calculation of an optical rotation angle by the sample 106, an output processing for outputting the optical rotation angle by the sample 106, an arithmetic processing for calculation of a concentration of an optically active material contained in the sample 106, e.g., a saccharide, an amino acid, a protein, or a vitamin.

The liquid crystal driver 109 supplies a predetermined bias voltage to the liquid crystal elements 104A and 104B. In addition, the liquid crystal driver 109 supplies a modulation voltage having predetermined amplitude and superimposed on the predetermined bias voltage to one of the liquid crystal elements 104A and 104B.

(Arrangement Configuration of Liquid Crystal Elements)

Figure 2:
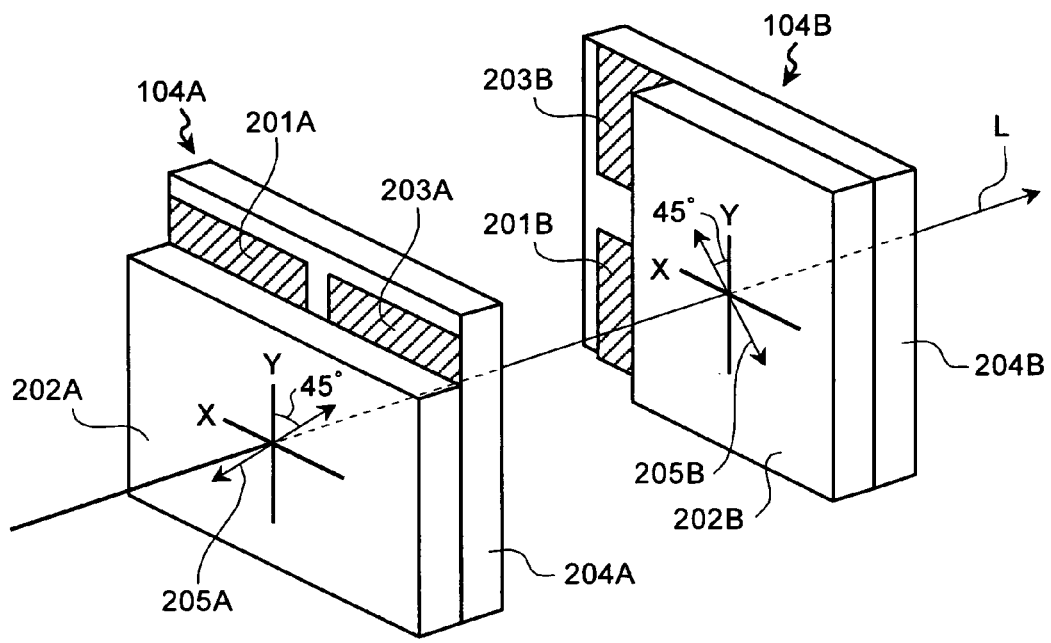
FIG. 2 is an explanatory diagram of an arrangement configuration of two liquid crystal elements shown in FIG. 1.

An arrangement configuration of the liquid crystal elements 104A and 104B shown in FIG. 1 will be explained specifically. FIG. 2 is an explanatory diagram of the arrangement configuration of the liquid crystal elements 104A and 104B shown in FIG. 1. In FIG. 2, the liquid crystal elements 104A and 104B are arranged in series on an optical path L. This optical path L is a route of the light from the light source 101 to the photodiode 107.

The liquid crystal element 104A is a homogeneous alignment-type liquid crystal element that includes a counter substrate 202A having a counter substrate input electrode 201A, and an electrode substrate 204A having an electrode substrate input electrode 203A. A liquid crystal, not shown, is provided between the counter substrate 202A and the electrode substrate 204A. The counter substrate input electrode 201A and the electrode substrate input electrode 203A are electrically connected to the liquid crystal driver 109 shown in FIG. 1. It is assumed that on a plane orthogonal to the optical path L that represents an incident direction, an axis representing the horizontal direction is an X axis, and an axis orthogonal to the X axis on the plane is a Y axis. The polarization axis 205A that represents an orientation direction of the liquid crystal element 104A is rotated clockwise by 45 degrees with respect to the Y axis.

Likewise, the liquid crystal element 104B is a homogeneous alignment-type liquid crystal element that includes a counter substrate 202B having a counter substrate input electrode 201B, and an electrode substrate 204B having an electrode substrate input electrode 203B. A liquid crystal, not shown, is provided between the counter substrate 202B and the electrode substrate 204B. The counter substrate input electrode 201B and the electrode substrate input electrode 203B are electrically connected to the liquid crystal driver 109 shown in FIG. 1. The polarization axis 205B that represents an orientation direction of the liquid crystal element 104B is rotated counterclockwise by 45 degrees with respect to the Y axis.

The counter substrate 202B of the liquid crystal element 104B is opposed to the electrode substrate 204A of the liquid crystal element 104A. Namely, the liquid crystal element 104B is a liquid crystal element obtained by rotating the same liquid crystal element as the liquid crystal element 104A by 90 degree. The polarization axis 205A that is the orientation direction of the liquid crystal element 104A is orthogonal to the polarization axis 205B that is the orientation direction of the liquid crystal element 104B.

Accordingly, the light-flux emitted from the light source 101 is transformed into the linearly polarized light by the polarizer 102A. The linearly polarized light is incident on the azimuth rotator 103 which slightly rotates the polarization plane of the component. The azimuth rotator 103 includes the liquid crystal elements 104A and 104B and the quarter-wave plate 105, and is driven by the liquid crystal driver 109. The transmission light slightly rotated by the azimuth rotator 103 is incident on the sample 106, transmitted by the polarizer 102B, and converted into the electric signal, i.e., sample signal according to the light intensity by the photodiode 107 that functions as a photoelectric converter.

The liquid crystal elements 104A and 104B employed as constituent elements of the azimuth rotator 103 are both homogeneous alignment-type liquid crystal elements having all the major axes of liquid crystal molecules aligned in parallel. If no voltage is applied between upper and lower electrodes, the liquid crystal molecules are aligned in parallel to a glass substrate. The liquid crystal molecules have refractive index anisotropy, so that the polarized component parallel to the major axes of the liquid crystal molecules and that parallel to the minor axes thereof differ in refractive index by $\Delta n$. If a voltage is applied between the upper and lower electrodes, then the liquid crystal molecules stand upright along an electric field and function as variable voltage doubly-refracting elements.

If a linearly polarized light inclined by 45 degrees with respect to the liquid crystal orientation direction is applied to the liquid crystal elements 104A and 104B, a phase difference $2\pi\Delta n \cdot d/\lambda$ (where d denotes a thickness of a liquid crystal layer and $\lambda$ denotes a wavelength) is generated between an electric field component parallel to the major axes of the liquid crystal molecules and that perpendicular to the electric field component in the incident linearly polarized light. As a result, a polarization state of the light is changed, so that the linearly polarized light is changed to the elliptically polarized light.

At this moment, the polarization axes 205A and 205B of the two liquid crystal elements 104A and 104B are orthogonal to each other. Assuming that phase modulation amounts of the two liquid crystal elements 104A and 104B are $2\pi \cdot \Delta n1 \cdot d/\lambda$ and $\Delta n2 \cdot d/\lambda$, respectively, a retardation given to the transmission light, that is, a phase difference between the polarized components orthogonal to each other is $2\pi(\Delta n1 - \Delta n2) \cdot d/\lambda$.

Furthermore, an azimuth angle of the elliptically polarized light is parallel (or orthogonal) to the incident linearly polarized light. If the retardation is equal to or smaller than $\lambda/2$, an elliptical axis of the elliptically polarized light coincides with the axis of the incident linearly polarized light. If one coordinate axis is set so as to coincide with the elliptical axis, the phase difference of the electric field components between coordinate axes orthogonal to each other is always $\pi$ (rad). By arranging the quarter-wave plate 105, therefore, the elliptically polarized light can be transformed into the linearly polarized light. At this moment, the polarization plane is rotated by an angle proportional to the total retardation given by the liquid crystal elements 104A and 104B, thereby operating as the azimuth rotator 103.

(Phase Modulation Characteristic of Liquid Crystal Element)

Figure 3:
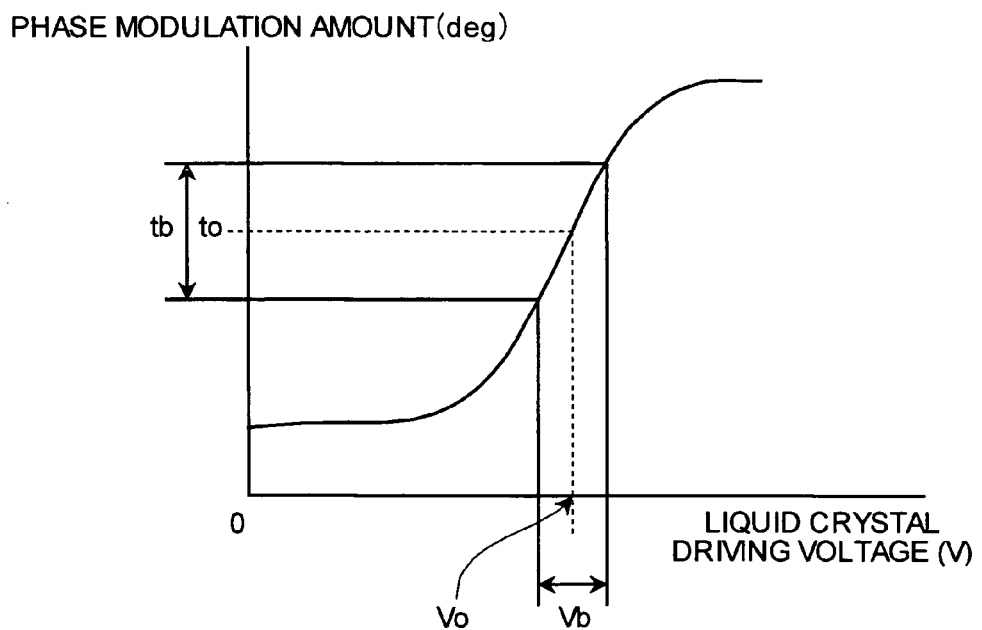
FIG. 3 is a graph of a phase modulation characteristic of the liquid crystal element.

A phase modulation characteristic of the liquid crystal element will be explained. FIG. 3 is a graph of the phase modulation characteristic of the liquid crystal element. In FIG. 3, the horizontal axis indicates a liquid crystal driving voltage supplied from the liquid crystal driver 109 and the vertical axis indicates a phase modulation amount of the linearly polarized light incident on the liquid crystal element 104 (104A or 104B). A curve is a phase modulation characteristic curve of the liquid crystal element 104 (104A or 104B).

Normally, the modulation characteristic of the liquid crystal element is that as shown in FIG. 3, and a liquid crystal molecule standing region of the liquid crystal element operates unstably and, at the same time, is non-linear to the driving voltage. It is, therefore, preferable to drive the liquid crystal element at a voltage near an offset voltage Vo. However, even if a desired phase modulation amount 'tb' is to be obtained, a phase modulation amount 'to' corresponding to the offset voltage Vo is superimposed on the phase modulation amount 'tb' as an unnecessary offset amount.

Considering this, the liquid crystal element that performs modulation is configured by the two liquid crystal elements (the liquid crystal elements 104A and 104B), the liquid crystal orientation directions of which are made orthogonal to each other. FIG. 4 is an explanatory diagram of a case that the driving voltage is applied to the liquid crystal elements 104A and 104B, the liquid crystal orientation directions of which are orthogonal to each other. In FIG. 4, the vertical axis indicates the driving voltage and the horizontal axis indicates time. To prevent polarization, the liquid crystal elements 104A and 104B are driven not by a DC voltage but an AC voltage having so high frequency that the liquid crystal molecules cannot respond to the applied voltage. The phase modulation amount is changed to correspond to an envelope of the driving signal.

A waveform 401 is obtained when the bias DC voltage (also referred to as "offset voltage") Vo and the AC voltage Vb having a predetermined amplitude are applied to one of the liquid crystal elements 104A and 104B. A waveform 402 is a waveform obtained when only the offset voltage Vo is applied to the other liquid crystal element. A waveform 403 is a waveform obtained from the waveforms 401 and 402.

The waveforms 401 and 402 can be obtained by modulating the liquid crystal elements 104A and 104B by the offset voltage Vo and modulating one of the liquid crystal elements 104A and 104B by the AC voltage Vb having the predetermined amplitude. By causing the waveforms 401 and 401 to offset each other, i.e., by removing the unnecessary offset amount of the waveform 401 corresponding to the offset voltage Vo from the waveform 402, the phase modulation amount 'to' corresponding to the offset voltage Vo can be cancelled. As shown in the waveform 403, only the desired phase modulation amount 'tb' can be obtained.

Even if the modulation characteristics of the liquid crystal elements are changed according to an external environmental change such as a temperature change, fluctuations in the elements can cancel each other by manufacturing the liquid crystal elements 104A and 104B according to the same specifications. This is because the liquid crystal elements 104A and 104B undergo the same characteristic change and have liquid crystal orientation directions orthogonal to each other.

It is assumed herein that the liquid crystal elements 104A and 104B are driven by the same voltage. If the phase modulation amount of the one liquid crystal element 104A (or 104B) is increased by ΔP at this same voltage, that of the other liquid crystal element 104B (or 104A) is similarly increased by ΔP. Since the phase modulation amounts ΔP are added to the respective liquid crystal elements by the orthogonal components thereof, the increased phase modulation amount ΔP of the liquid crystal element 104A and that of the liquid crystal element 104B offset each other. Accordingly, the polarization state is not changed, so that the influence of the modulation on the measurement result can be cancelled.

If one liquid crystal element is employed and a linear part of the modulation characteristic (curve) of the liquid crystal element shown in FIG. 3 is used, the DC voltage Vo is simultaneously applied to the element with the AC voltage Vb for obtaining the desired phase modulation amount 'tb'. Due to this, unnecessary modulation of the polarization state is applied to the element, with the result that the stability of the liquid crystal element is deteriorated.

Furthermore, the arrangement of the optical element on which the light-flux emitted from the liquid crystal element and an optical axis direction of the light-flux emitted from the liquid crystal element are determined by the polarization state of the light-flux emitted from the liquid crystal element. It is, therefore, necessary to set the polarization state of the light-flux emitted from the liquid crystal element in advance. At this time, the unnecessary modulation amount given by the offset voltage Vo makes it difficult to set the polarization state of the light-flux emitted from the liquid crystal element. To obtain the desired polarization state, therefore, it is difficult to design the liquid crystal element and high manufacturing accuracy is required. For example, a polarization axis of the polarizer 102B arranged in front of the photodiode 107 that functions as the photoelectric converter is preferably orthogonal to the light axis of the emitted linearly polarized light.

As can be seen, by canceling the influence of the fluctuations in the liquid crystal element, measurement data can be stabilized and improvement of the measurement accuracy can be expected. Besides, by canceling the influence of the fluctuations in the liquid crystal element, it is possible to easily design the optical system and the liquid crystal element. The manufacturing accuracy can be, therefore, relaxed.

Figure 5A:
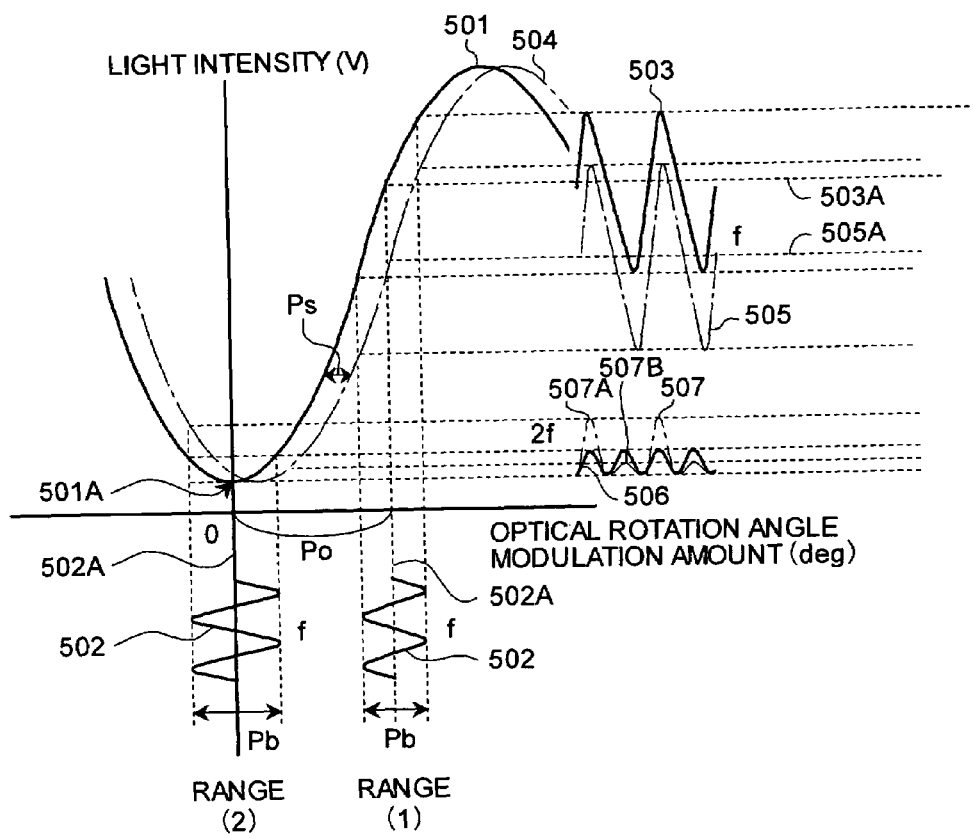
FIG. 5A is a graph of the relationship between a modulation amount of an optical rotation angle made by an azimuth rotator and a light intensity detected by a photodiode.
Figure 5B:
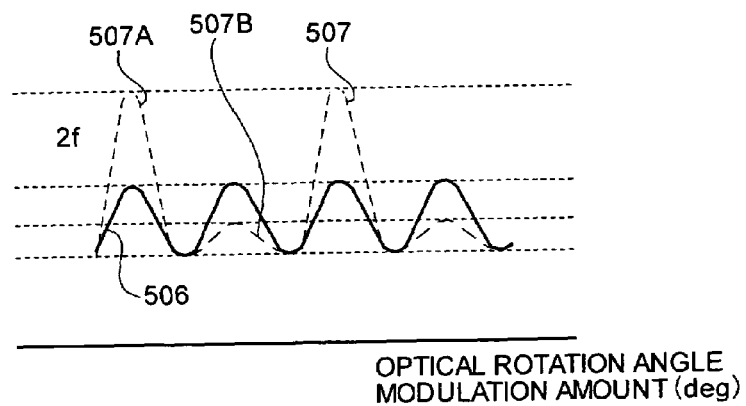
FIG. 5B is a partially enlarged view of FIG. 5A.

The relationship between the optical rotation angle modulation amount of the light the polarization plane of which is rotated by the azimuth rotator 103 and the light intensity detected by the photodiode 107 will next be explained. FIG. 5A is a graph of the relationship between the optical rotation angle modulation amount of the light the polarization plane of which is rotated by the azimuth rotator 103 and the light intensity detected by the photodiode 107. FIG. 5B is a partially enlarged view of FIG. 5A. In FIG. 5A, waveforms 501, 502, and 503 indicated by solid lines are those obtained when the sample 106 is absent, and waveforms 504, 505, and 506 indicated by one-dot chain lines are those obtained when the sample 106 is present.

The light intensity is changed relative to the modulation amount of the optical rotation angle as shown in the large sinusoidal wave 501 shown in FIG. 5A. If only one liquid crystal element is provided and the offset voltage Vo and the AC voltage Vb having the predetermined amplitude are applied to the one liquid crystal element, then a vibration center 502A of the modulation frequency signal 502 at the modulation frequency f of the liquid crystal element is offset from a minimum 501A by as much as an optical rotation angle Po corresponding to the phase modulation amount (also referred to as "offset amount") 'to' by which the liquid crystal element is modulated. With this rotation angle Po as the vibration center, the modulation frequency signal 502 is modulated in a range of an optical rotation angle width Pb corresponding to the phase modulation amount 'tb' given by the AC voltage Vb having the predetermined amplitude shown in FIG. 3, e.g., in a range (1) of FIG. 5A.

If the modulation frequency signal 502 is modulated in this range (1), a signal waveform obtained from the photodiode 107 is equal to the signal waveform 503 at the frequency f in a state in which the sample 106 is absent. If the sample 106 is provided, the sinusoidal wave 501 is changed to the sinusoidal wave 504 offset from the waveform 502 by as much as an optical rotation angle Ps.

In this case, even if a vibration center 503A of the signal waveform 503 at the frequency f is offset to a vibration center 505A by the optical rotation angle Ps by the sample 106, the obtained signal waveform 505 is changed only in the magnitude of a DC component from the signal waveform 503. However, the influence of the fluctuation in the intensity of the light source cannot be separated from that of the fluctuation in the transmissivity of the sample 106. The optical rotation angle Ps by the sample 106, therefore, includes an error corresponding to the fluctuation in the intensity of the light source.

It is, therefore, necessary to make the vibration center 502A of the modulation frequency signal 502 coincident with the minimum 501A. In addition, it is necessary that the phase modulation amount 'to' corresponding to the offset voltage Vo is precisely an integer multiple of $2\pi$. As a result, requirements for the liquid crystal element including a requirement to increase the phase modulation width and a requirement to accurately reproduce an absolute value of the phase modulation amount are stricter.

An instance of providing the two liquid crystal elements will be considered. For example, the phase modulation is performed on the liquid crystal elements while the waveform of the offset voltage Vo to be applied to the liquid crystal element 104A is changed to a sinusoidal waveform by as much as the amplitude of the AC voltage Vb (see the waveform 401 shown in FIG. 4). The liquid crystal element 104B performs the phase modulation by the offset voltage Vo (see the waveform 402 shown in FIG. 4). The azimuth rotator 103 can be thereby driven to vibrate the polarization plane slightly in a sinusoidal manner with the optical rotation angle made to correspond to the amplitude of the AC voltage Vb (see the waveform 403 shown in FIG. 4).

With the sample 106 absent, the polarizers 102A and 102B are arranged so that the transmission axes thereof are orthogonal to each other and the amplitude center 502A of the modulation range is made coincident with the minimum 501A of the sinusoidal wave 501. In addition, the modulation frequency of the liquid crystal elements is set to f. If so, the modulation frequency signal 502 can be modulated in a range (2) shown in FIG. 5A and the signal 506 at a frequency 2f can be obtained.

If the sample 106 is present and the rotation is made by the sample 106, the center 502A of the modulation range is slightly offset from the minimum 501A and the signal waveform 506 is changed to the signal waveform 507. In this signal waveform 507, adjacent wave heights 507A and 507B are different. Therefore, this signal waveform 507 is A/D converted into a digital signal and the digital signal is input to the arithmetic processor 108, whereby the optical rotation angle by the sample 106 can be calculated. A typical method for calculating the optical rotation angle is synchronous detection at the frequency 2f. Alternatively, the optical rotation angle can be calculated based on amplitude of the signal waveform 507, that is, a wave height ratio of the wave height 507A to the wave height 507B.

It is assumed herein that the modulation amount of the liquid crystal element 104A is increased by $\Delta P$ due to an atmospheric pressure change or the like. If so, the modulation amount of the liquid crystal element 104B is similarly increased by $\Delta P$. Since the liquid crystal orientation directions of the liquid crystal elements 104A and 104B are orthogonal to each other, the fluctuations in the modulation amounts thereof cancel each other. By canceling the offset amount 'to', the modulation amount of the liquid crystal elements is equal to the minimum, thereby making it possible to easily determine the arrangement of the optical axes of the optical components other than the liquid crystal elements.

(Hardware Configuration of Arithmetic Processor)

Figure 6:
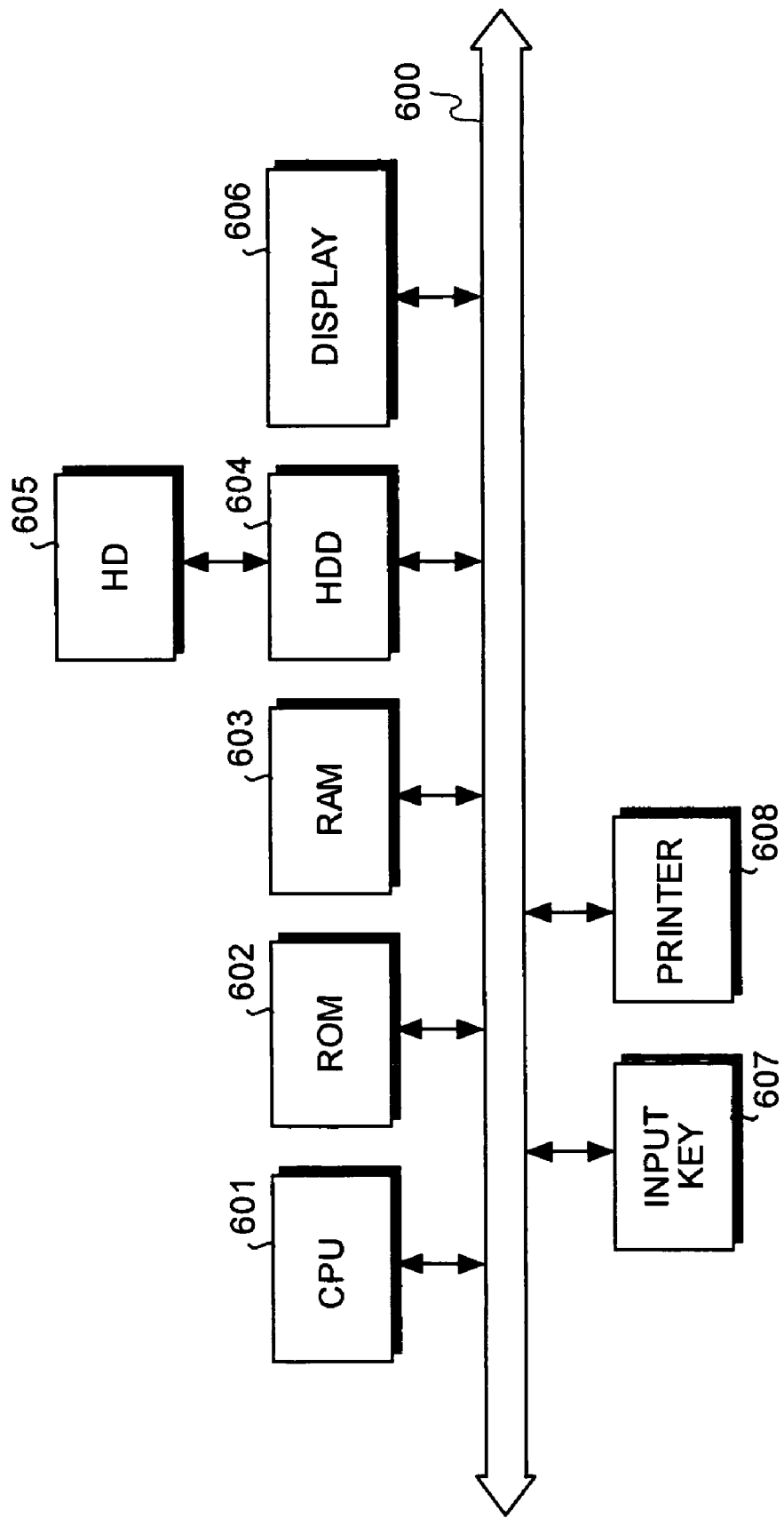
FIG. 6 is a block diagram of a specific hardware configuration of an arithmetic processor shown in FIG. 1.

A specific hardware configuration of the arithmetic processor 108 shown in FIG. 1 will be explained. FIG. 6 is a block diagram of the specific hardware configuration of the arithmetic processor 108 shown in FIG. 1.

In FIG. 6, the arithmetic processor 108 includes a CPU 601, a ROM 602, a RAM 603, a HDD (hard disk drive) 604, a HD (hard disk) 605, a display 606, input keys 607, and a printer 608. The respective constituent elements of the arithmetic processor 108 are mutually connected by a bus 600.

The CPU 601 controls the entire arithmetic processor 108. The ROM 602 stores programs such as a boot program. The RAM 603 is used as a work area for the CPU 601. The HDD 604 controls data to be read and written from and to the HD 605 under control of the CPU 601. The HD 605 stores the data written under control of the HDD 604.

The display 606 displays data such as a document, an image, and functional information as well as a cursor, an icon, and a tool box. As this display 606, a CRT, a TFT liquid crystal display, or a plasma display, for example, can be employed.

The input keys 607 are keys for inputting characters, numbers, various instructions, and the like. The input keys 607 can be a touch panel type input pad, ten (number) keys, or the like. The printer 608 prints image data and document data. As the printer 608, a laser printer or an inkjet printer, for example, can be employed.

(Functional Configuration of Optical Rotation Angle Measuring Apparatus)

Figure 7:
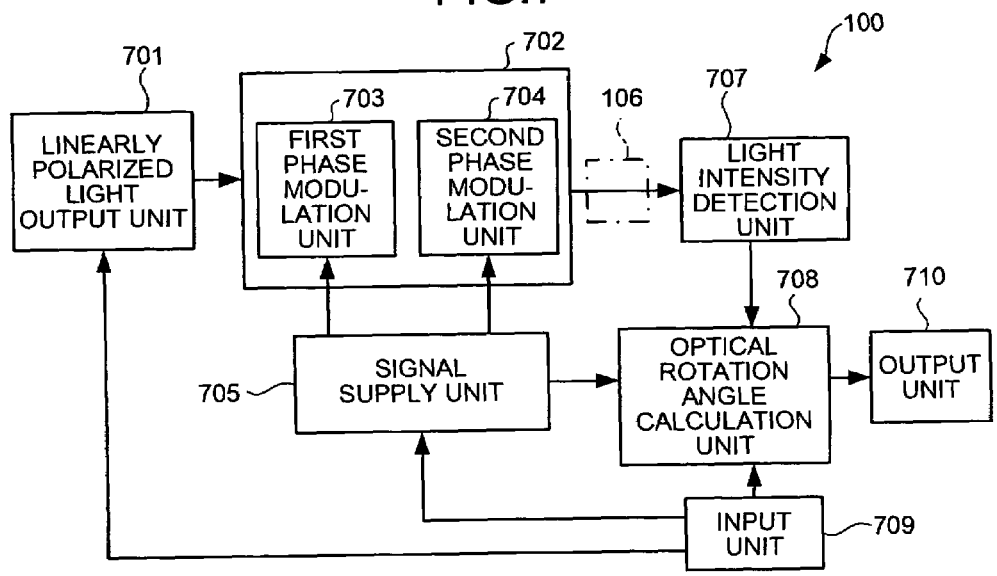
FIG. 7 is a block diagram of a functional configuration of the optical rotation angle measuring apparatus according to the first embodiment to a sixth embodiment of the present invention.

A functional configuration of the optical rotation angle measuring apparatus according to first to sixth embodiments of the present invention will be explained. FIG. 7 is a block diagram of the functional configuration of the optical rotation angle measuring apparatus according to the first to the sixth embodiments of the present invention. In FIG. 7, the optical rotation angle measuring apparatus 100 includes a linearly polarized light output unit 701, a phase modulation unit 702, a signal supply unit 705, a light intensity detection unit 707, an optical rotation angle calculation unit 708, an input unit 709, and an output unit 710.

The linearly polarized light output unit 701 outputs a linearly polarized light. Specifically, the function of this linearly polarized light output unit 701 is realized by, for example, the light source 101 and the polarizer 102A shown in FIG. 1.

The phase modulation unit 702 includes a first phase modulation unit 703 and a second phase modulation unit 704. The first phase modulation unit 703, which includes a first polarization axis in a predetermined direction, modulates a phase of the linearly polarized light output from the linearly polarized light output unit 701. The function of this first phase modulation unit 703 is realized by the liquid crystal element 104A shown in FIG. 1. In addition, the second phase modulation unit 704, which includes a second polarization axis orthogonal to the first polarization axis, modulates the phase of the linearly polarized light output from the linearly polarized light output unit 701. Specifically, the function of the second phase modulation unit 704 is realized by the liquid crystal element 104B shown in FIG. 1. Accordingly, a direction of the first polarization axis corresponds to the orientation direction 205A whereas a direction of the second polarization axis corresponds to the orientation direction 205B.

The signal supply unit 705 supplies a modulation signal having a predetermined amplitude for modulating the phase of the linearly polarized light to one of the first phase modulation unit 703 and the second phase modulation unit 704. Specifically, this modulation signal having the predetermined amplitude is, for example, the AC voltage Vb having the predetermined amplitude shown in FIG. 3.

The signal supply unit 705 also supplies a predetermined bias signal to both the first phase modulation unit 703 and the second phase modulation unit 704. Specifically, this bias signal having the predetermined amplitude is, for example, the offset voltage Vo shown in FIG. 3. Specifically, the function of this signal supply unit 705 is realized by, for example, the liquid crystal driver 109 shown in FIG. 1.

The light intensity detection unit 707 detects an intensity of the transmission light by causing the polarization plane of the light emitted from the first phase modulation unit 703 and second phase modulation unit 704, to which the signal is supplied from the signal supply unit 705, to the sample 106 containing the optical active materials to be rotated by the optically active materials and the light to be transmitted by the sample 106.

Specifically, the function of this light intensity detection unit 707 is realized by, for example, the photodiode 107 shown in FIG. 1. In addition, a PN junction device of silicon semiconductors biased in opposite directions, a phototransistor element, a cadmium sulfide photoconductive element or the like can be used as well as the photodiode 107.

The optical rotation angle calculation unit 708 calculates the optical rotation angle by the sample 106 based on the modulation signal supplied from the signal supply unit 705 and the light intensity detected by the light intensity detection unit 707. Specifically, the optical rotation angle calculation unit 708 calculates the optical rotation angle by the sample 106 based on the wave height ratio of the wave height 507A to the wave height 507B of the signal waveform 507 shown in FIG. 5A, using an arithmetic equation for calculating the optical rotation angle or a correlation table that indicates the correlation between this wave height ratio and the optical rotation angle.

That is, by measuring the phase modulation characteristic of the liquid crystal elements in advance, the phase modulation width Pb of the liquid crystal elements by the liquid crystal driving voltage Vb is known. It is, therefore, possible to strictly calculate a change in the wave height ratio according to the optical rotation angle by the sample 106 using an equation. Conversely, it is possible to obtain the arithmetic equation for calculating the optical rotation angle by the sample 106 from the wave height ratio. More practically, a working curve that indicates the correlation between the concentration and the wave height ratio is calculated in advance using the sample a specific rotation angle for which is known, and the concentration of the sample can be calculated according to the wave height ratio using this working curve.

Specifically, the function of this optical rotation angle calculation unit 708 is realized by, for example, allowing the CPU 601 to execute a program stored in the ROM 602 or the RAM 603 shown in FIG. 6.

The input unit 709 performs an input processing for the supply of the DC power to the laser diode included in the light source 101 shown in FIG. 1, an input processing for the driving of the liquid crystal driver 109, an input processing for the calculation of the optical rotation angle by the sample 106. Specifically, the function of this input unit 709 is realized by, for example, the input keys 607 shown in FIG. 6.

The output unit 710 outputs the optical rotation angle by the sample 106 calculated by the optical rotation angle calculation unit 708. Specifically, the function of this output unit 710 is realized by, for example, the display 606 or the printer 608 shown in FIG. 6.

As explained so far, the first embodiment exhibits an advantage in that the optical rotation angle by the sample 106 can be accurately measured by using the small-sized liquid crystal elements 104 (104A and 104B) that can be driven at the lower power consumption as the modulation elements.

In addition, the first embodiment exhibits advantages in that the modulation can be modulated by as much as the very small modulation width Vb and the highly accurate measurement can be ensured by using the driving voltage range in which the modulation characteristics of the liquid crystal elements 104 (104A and 104B) are stable, i.e., by using the offset voltage Vo.

Furthermore, the first embodiment exhibits advantages in that the liquid crystal elements 104 (104A and 104B) can be easily designed and the manufacturing accuracy can be relaxed since the requirements of the modulation range and the absolute value of the modulation amount for the liquid crystal elements 104 (104A and 104B) can be relaxed.

Furthermore, the first embodiment exhibits advantages in that the fluctuations in the liquid crystal elements 104 (104A and 104B) caused by the external environment can be cancelled, the measurement result can be stabilized, and the measurement accuracy can be improved.

Second Embodiment

Figure 8:
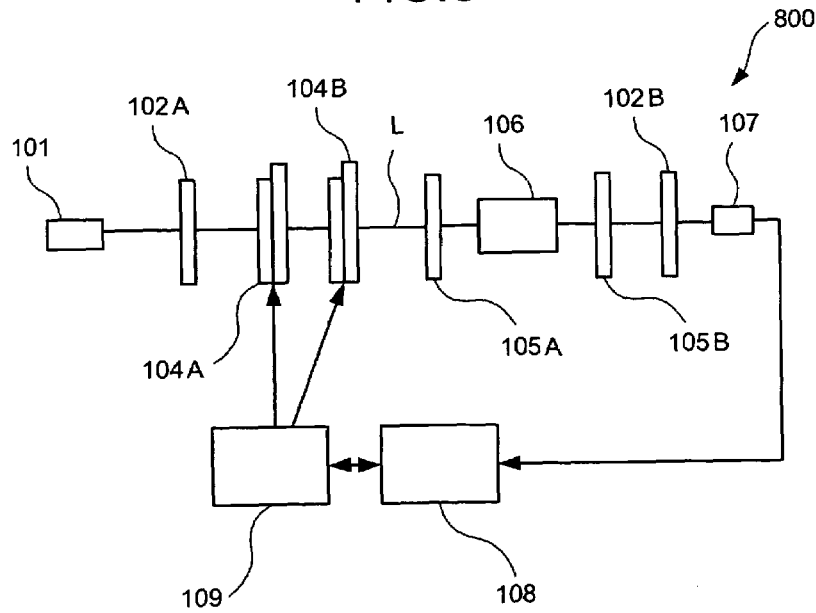
FIG. 8 is a block diagram of a hardware configuration of the optical rotation angle measuring apparatus according to a second embodiment of the present invention.

A second embodiment of the present invention will be explained. FIG. 8 is a block diagram of a hardware configuration of an optical rotation angle measuring apparatus according to the second embodiment of the present invention. An optical rotation angle measuring apparatus 800 according to the second embodiment is configured so that the sample 106 is held between two quarter-wave plates 105A and 105B on the optical path L. In FIG. 8, like constituent elements as those in the hardware configuration shown in FIG. 1 are denoted by like reference symbols.

FIG. 8 is a block diagram of the second embodiment. A light-flux emitted from the light source 101 is transformed into a linearly polarized light by the polarizer 102A. The liquid crystal elements 104A and 104B are arranged next to the polarizer 102A. As the liquid crystal elements 104A and 104B, homogenous alignment-type liquid crystal elements are employed. The liquid crystal molecule orientation directions of the liquid crystal elements 104A and 104B are orthogonal to each other at angles of ±45 degrees with respect to the polarization axis of the incident linearly polarized light, respectively. If a driving voltage is applied to the liquid crystal elements 104A and 104B, the elements 104A and 104B can operate as the phase modulation units that give the phase difference between the polarized components orthogonal to each other.

Accordingly, the incident linearly polarized light is transformed into an elliptically polarized light. If the phase modulation amount is larger, ellipticity is lower. At the phase difference of $\pi/2$, the elliptically polarized light is transformed into a circularly polarized light. If the modulation amount is made larger, the circularly polarized light is transformed into an elliptically polarized light orthogonal to the incident linearly polarized light. At the phase difference of $\pi$, the elliptically polarized light is transformed into the linearly polarized light again. Therefore, if the light intensity is observed through the polarizer having the transmission axis parallel to the incident linearly polarized light, it is seen that a signal having a sinusoidal waveform repeating rise and fall per phase difference $2\pi$ (rad) is obtained.

The linearly polarized light is then transmitted by the quarter-wave plate 105A and incident on the sample 106. The two polarized components orthogonal to each other and modulated by the liquid crystal elements 104A and 104B are transformed into a clockwise circularly polarized light and a counterclockwise circularly polarized light by the quarter-wave plate 105A, respectively. The rotation of the polarization plane of the light is made by a difference in refractive index between the clockwise circularly polarized light and the counterclockwise circularly polarized light. Due to this, the respective circularly polarized lights are subjected to phase modulations according to the optical rotation angles by the sample 106. As a result, at the optical rotation angle of θ (rad), a phase difference of 2θ (rad) is generated between the two polarized components.

The lights are then transmitted by the quarter-wave plate 105B, thereby transforming the clockwise circularly polarized light and counterclockwise circularly polarized light the phases of which are modulated by the sample 106 into linearly polarized lights orthogonal to each other. These two linearly polarized lights are transmitted by the polarizer 102B inclined by 45 degrees with respect to the polarization direction of the lights. By doing so, the phase modulation amount is transformed into a light intensity and the light intensity is converted into an electric signal by the photodiode 107.

As can be seen, according to the second embodiment, the same signal as that according to the first embodiment can be obtained. Using the obtained signal, the optical rotation angle by the sample 106 can be calculated. If two liquid crystal elements are employed as the modulation elements and the liquid crystal orientation directions of the elements are made orthogonal to each other, then the offset amounts can cancel each other similarly to the first embodiment, the same advantages as those of the first embodiment can be attained, and the measuring accuracy can be similarly improved. For the same reasons as those for the liquid crystal elements, by making optical axes of the two quarter-wave plates orthogonal to each other, fluctuations in characteristics of the quarter-wave plates due to the temperature, humidity or the like can cancel each other. The measuring accuracy can be, therefore, improved.

Third Embodiment

Figure 9:
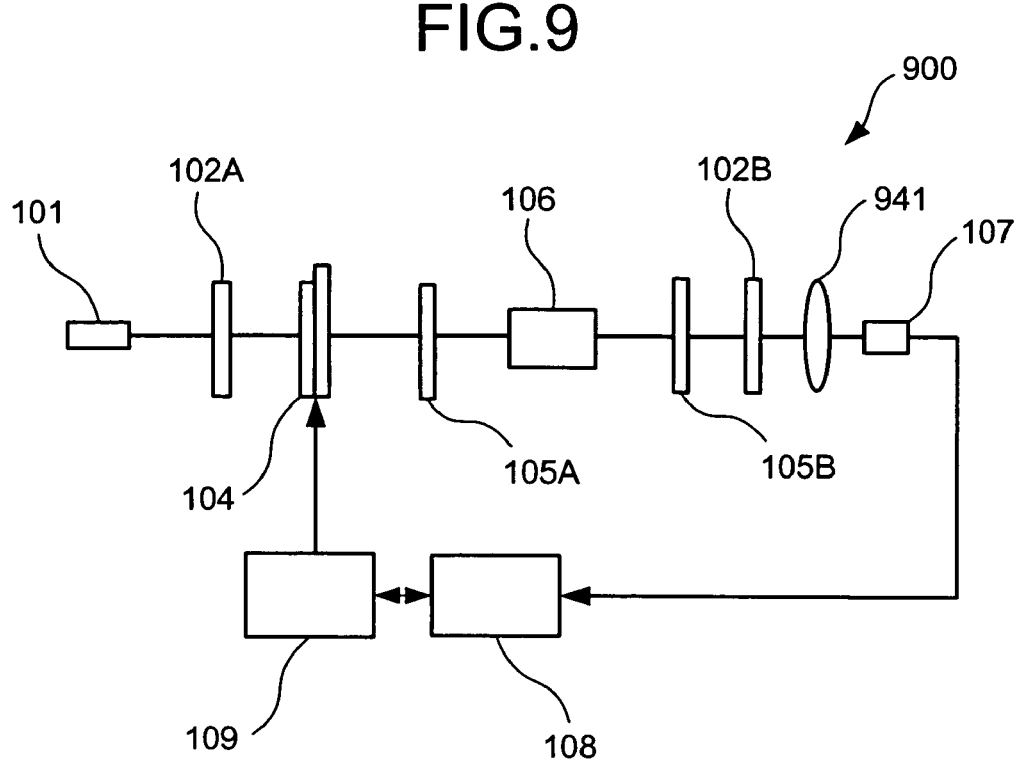
FIG. 9 is a block diagram of a hardware configuration of the optical rotation angle measuring apparatus according to a third embodiment of the present invention.

A third embodiment of the present invention will be explained. FIG. 9 is a block diagram of a hardware configuration of an optical rotation angle measuring apparatus according to the third embodiment of the present invention. The two liquid crystal elements 104A and 104B are employed in the optical rotation angle measuring apparatus 800 according to the second embodiment. One liquid crystal element 104 is employed in an optical rotation angle measuring apparatus 900 according to the third embodiment, and the liquid crystal element 104 has a pixel structure. A lens 941 serving as a condensing unit is additionally provided in the apparatus 900, and the photodiode 107 is arranged on a focal plane of the lens 941. In FIG. 9, like constituent elements as those in the hardware configurations shown in FIGS. 1 and 8 are denoted by like reference symbols.

Figure 10A:
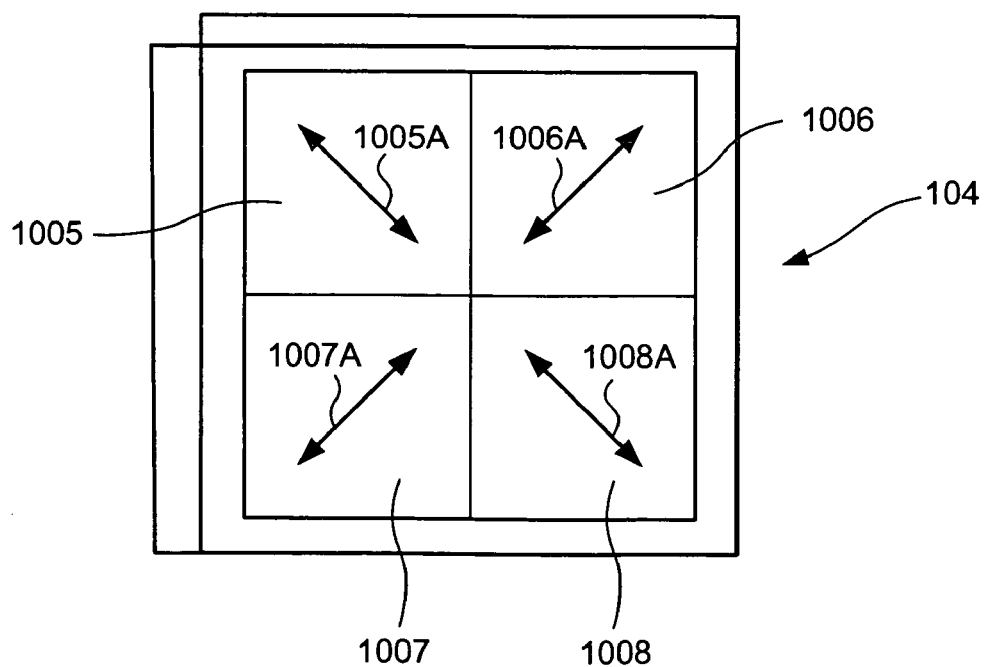
FIG. 10A is a front view of a liquid crystal element.

The liquid crystal element 104 is configured by a plurality of pixels 1005 to 1008 (four pixels in FIG. 10A). FIG. 10A is a front view of the liquid crystal element 104. FIG. 10A shows the liquid crystal element 104 configured by, for example, four pixels. In FIG. 5A, arrows indicate orientation directions 1005A to 1008A of respective pixels 1005 to 1008 that constitute the liquid crystal element 104. The orientation directions 1005A to 1008A are configured to be orthogonal to one another. Specifically, the orientation directions of the two pixels adjacent in a vertical or horizontal direction are orthogonal to each other, and those of the pixels in a diagonal direction are parallel to each other.

As means for changing the orientation directions of the respective pixels, a UV irradiation method is known. With this method, a UV is irradiated on the liquid crystal element 104 through an arbitrary mask, whereby orientation directions of regions irradiated with the UV are rotated. Rotation angles of the regions an be controlled by irradiation time and a certain region can be rotated by 90 degrees (see, for example, YAMAGUCHI Rumiko and SATO Susumu, "Orientation Patterning Characteristics by Azimuth Angle Anchoring Power Control", preliminary papers of Japanese Liquid Crystal Society Lecture Meeting, 2002, p. 119).

A driving signal applied to the liquid crystal element 104 is changed according to the orientation directions 1005A to 1008A of the respective pixels 1005 to 1008, and the signals applied to the liquid crystal elements 104A and 104B according to the first embodiment are applied thereto. For example, a signal obtained by superimposing the AC voltage Vb having the amplitude changed in a sinusoidal manner on the offset voltage Vo is applied to the pixels 1005 and 1008 having one orientation direction 1005A or 1008A. A signal of the offset voltage Vo is applied to pixels 1006 and 1007 having the other orientation direction 1006A or 1007A.

The light-flux transmitted by the liquid crystal element 104 is condensed by the lens 941. If the light-flux is not condensed by the lens 941, the different modulation signals according to the respective pixels 1005 to 1008 can be obtained. By condensing the light-flux using the lens 941, the signals interfere with one another on the photodiode 107 arranged on the focal plane of the lens 941 and the same signals as those when the liquid crystal elements 104A and 104B are arranged in series in the light irradiation direction can be obtained.

Figure 10B:
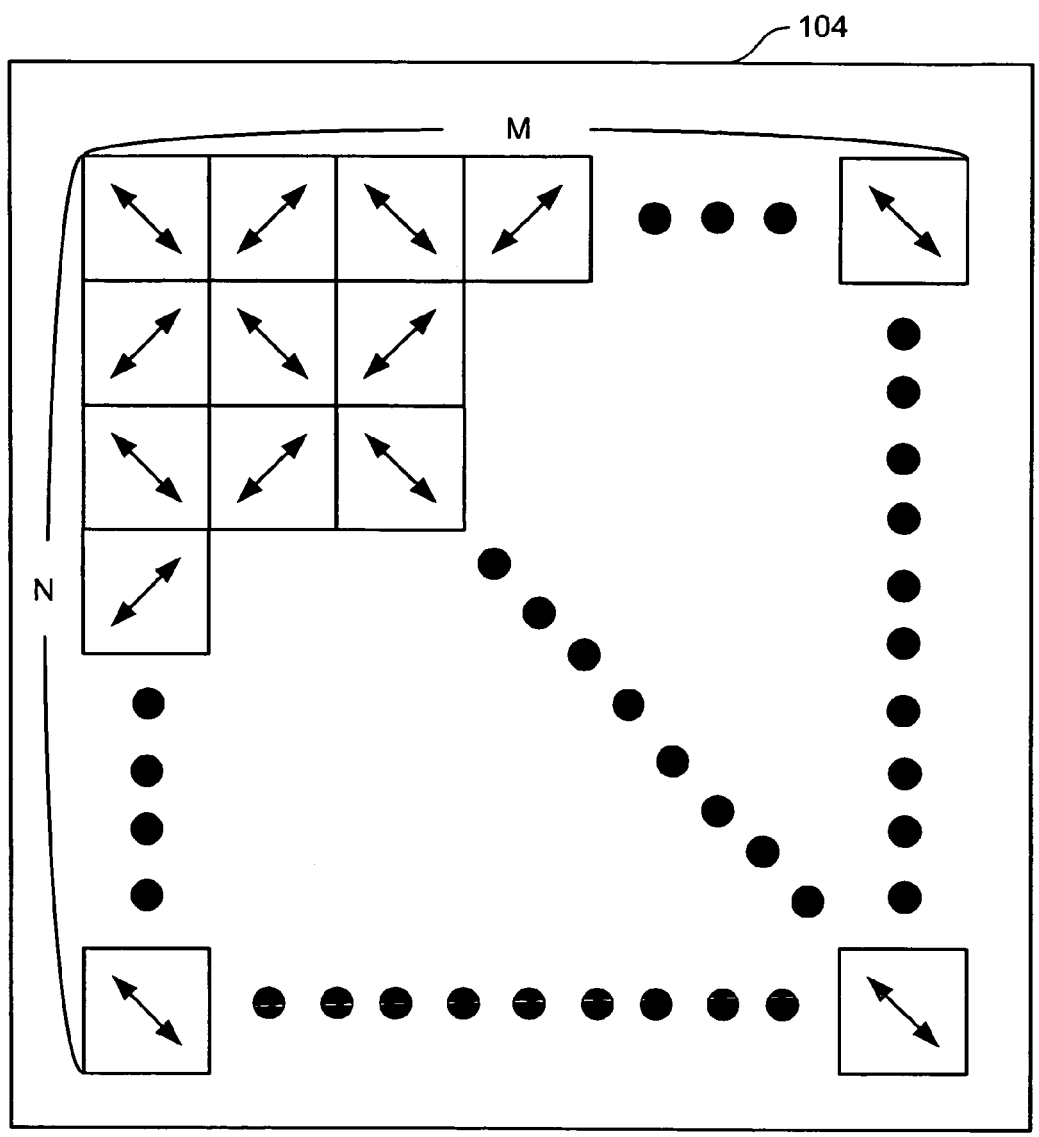
FIG. 10B is a front view of a liquid crystal element formed to have a finer pixel structure.

FIG. 10B is a front view of the liquid crystal element 104 a pixel structure of which is made finer. This liquid crystal element 104 has a N×M pixel structure. By configuring the liquid crystal element 104 to have the finer pixel structure and to allow light-fluxes of the pixels having orientation directions that are made orthogonal by pixel diffraction to interfere with one another instead of condensing the light-flux using the lens 941, the same advantages as those of the first and the second embodiment can be attained. In addition, by so configuring, it is unnecessary to arrange the lens 941, making it possible to reduce the number of components and make the optical rotation angle measuring apparatus smaller in size. Besides, it suffices to only make the pixel structure finer without the need to adjust a focal position of the lens 941, so that the measuring accuracy can be advantageously improved.

As can be seen, the optical rotation angle measuring apparatus according to one of the first to the third embodiments includes the light source, the azimuth rotator that modulates the light-flux from the light source, the polarizer that extracts the specific polarized components of the light-flux transmitted by the sample, and the photoelectric converter that converts the light intensity of the light-flux transmitted by the polarizer into the electric signal. The azimuth rotator is configured by the two liquid crystal elements and the quarter-wave plate, and the liquid crystal elements are arranged so that the liquid crystal molecule orientation directions of the respective elements are orthogonal to each other.

Furthermore, the optical rotation angle measuring apparatus according to one of the first to the third embodiments includes the light source, the phase modulation unit that modulates the light-flux from the light source, the two quarter-wave plates arranged in front of and in rear of the sample, respectively, the polarizer that extracts specific polarized components of the light-flux transmitted by the quarter-wave plates and the sample, and the photoelectric converter that converts the light intensity of the light-flux transmitted by the polarizer into the electric signal. The phase modulation unit is configured by two liquid crystal elements and the liquid crystal molecule orientation directions of the elements are orthogonal to each other.

The optical rotation angle measuring apparatus according to one of the first to the third embodiments includes the light source, the azimuth rotator that modulates the light-flux from the light source, the polarizer that extracts the specific polarized components of the light transmitted by the sample, and the photoelectric converter that converts the light intensity of the light-flux transmitted by the polarizer into the electric signal. The azimuth rotator is configured by the liquid crystal element and the quarter-wave plate, and the liquid crystal element is configured by a plurality of pixels the liquid crystal molecule orientation directions of which are orthogonal to one another.

The optical rotation angle measuring apparatus according to one of the first to the third embodiments includes the light source, the azimuth rotator that modulates the light-flux from the light source, the two quarter-wave plates arranged in front of and in rear of the sample, respectively, the polarizer that extracts the specific polarized components of the light transmitted by the sample and the quarter-wave plates, and the photoelectric converter that converts the light intensity of the light-flux transmitted by the polarizer into the electric signal. The phase modulation unit is the liquid crystal element configured by a plurality of pixels the liquid crystal molecule orientation directions of which are orthogonal to one another.

Hence, the influence of the fluctuations in the liquid crystal element can be cancelled, the measuring data can be stabilized, and the improvement of the measuring accuracy can be expected. In addition, it is possible to facilitate designing the optical system and the liquid crystal element, and to thereby relax the manufacturing accuracy.

Fourth Embodiment

A fourth embodiment of the present invention will be explained. FIG. 11 is a plan view of a liquid crystal substrate on which the liquid crystal elements employed in the optical measuring apparatus (the optical rotation angle measuring apparatus according to each of the first to the third embodiments of the present invention) is manufactured. According to this fourth embodiment, two arbitrary liquid crystal elements are cut out of a liquid crystal substrate 1100. This liquid crystal substrate 1100 is a substrate manufactured at well-known manufacturing steps. The two liquid crystal elements cut out of this liquid crystal substrate 1100 are equal in liquid crystal orientation direction and structure. If modulation characteristics of the two liquid crystal elements fluctuate according to an external environmental change such as a temperature change, fluctuations of the elements can cancel each other since the elements are orthogonal to each other.

If one of the liquid crystal elements cut out of the liquid crystal substrate 1100 is assumed as, for example, a liquid crystal element 1101, the other liquid crystal can be assumed as, for example, one of liquid crystal elements 1111 to 1113. Since the manufactured liquid crystal elements are cut out of the same liquid crystal substrate 1100, they are more closely akin in characteristics than the other liquid crystal elements manufactured on the liquid crystal substrate 1100. Accordingly, by arranging the two liquid crystal elements back to back, the fluctuations thereof can cancel each other.

Furthermore, the liquid crystal elements are preferably manufactured at positions proximate to each other. For example, if one of the two liquid crystal elements cut out of the liquid crystal substrate 1100 is the liquid crystal element 1101 shown in FIG. 11, the other liquid crystal element can be one near the liquid crystal element 1101, to be specific, one of liquid crystal elements 1102 to 1109 surrounding the liquid crystal element 1101. The liquid crystal elements 1102 to 1109 are closer to the liquid crystal element 1101 than liquid crystal elements 1111 to 1113 and the other liquid crystal elements on the liquid crystal substrate 1100. The liquid crystal element 1101 is, therefore, equal in characteristic to the liquid crystal elements 1102 to 1109. By arranging these liquid crystal elements back to back, the same fluctuations thereof can cancel each other.

Figure 12:
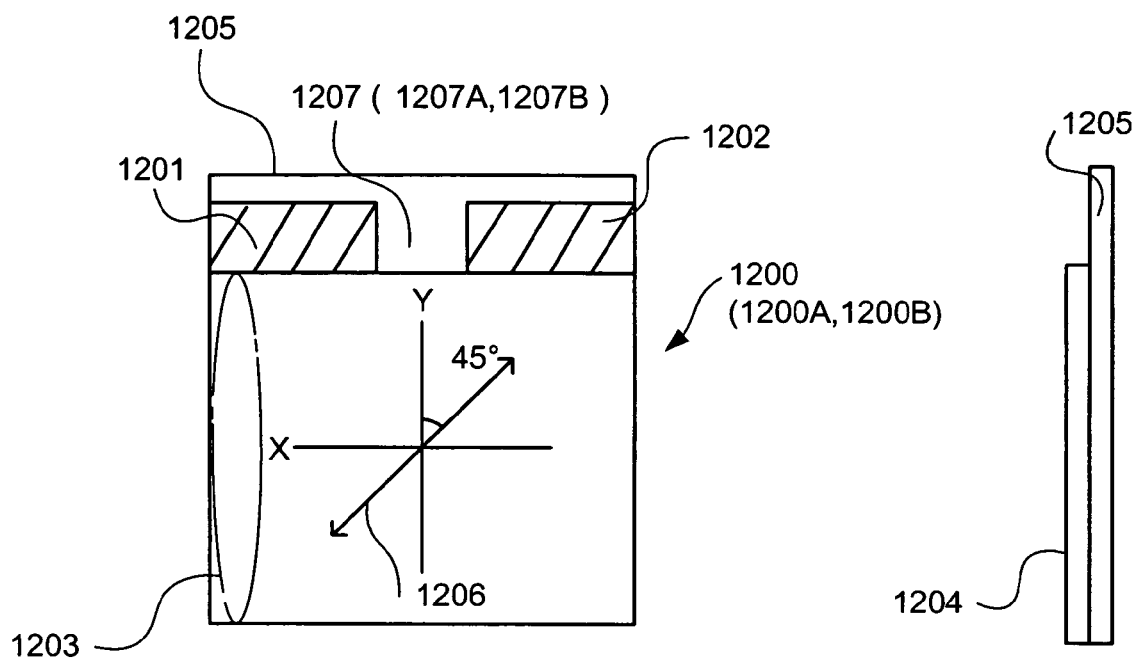
FIG. 12 is an external view of a liquid crystal element employed in the optical rotation angle measuring apparatus according to the first to the third embodiments of the present invention, that is, an optical measurement apparatus.

FIG. 12 is an external view of a liquid crystal element employed in the optical measuring apparatus (the optical rotation angle measuring apparatus according to the first to the third embodiments of the present invention). In FIG. 12, the drawing on the left is a plan view, and the one on the right figure is a side view.

A liquid crystal element 1200 is configured to hold a liquid crystal between a counter substrate 1204 and an electrode substrate 1205. By applying a voltage to an electrode (not shown) formed on the counter substrate 1204 and an electrode (not shown) formed on the electrode substrate 1205, a state of the liquid crystal is changed to thereby change a state of a light passing through the liquid crystal element 1200.

An electrode substrate input electrode 1202 is electrically connected to the electrode formed on the electrode substrate 1205. A counter substrate input electrode 1201 is electrically connected to the electrode formed on the counter substrate 1204 through conductive particles in an electrode transfer region 1203. The counter substrate input electrode 1201 and the electrode substrate input electrode 1202 are formed on an electrode cut-out surface 1207. It is assumed herein that on a plane orthogonal to the optical path L that represents an incident direction, an axis that represents a horizontal direction is the X axis and an axis orthogonal to the X axis is the Y axis. An orientation direction 1206 indicates that the liquid crystal is oriented in parallel to a direction at 45 degrees clockwise with respect to the Y axis.

While the optical rotation angle by the sample can be calculated using one liquid crystal element similarly to the conventional technique, if two liquid crystal elements are arranged in series and liquid crystal orientation directions of the elements are made orthogonal to each other, the optical rotation angle can be measured more accurately. Namely, if the modulation amount of one of the liquid crystal elements is increased by an external temperature change, atmospheric pressure change or the like, that of the other liquid crystal element is increased accordingly. Since the liquid crystal orientation directions of the two liquid crystal elements are orthogonal to each other, the fluctuations in the elements cancel each other.

Figure 13:
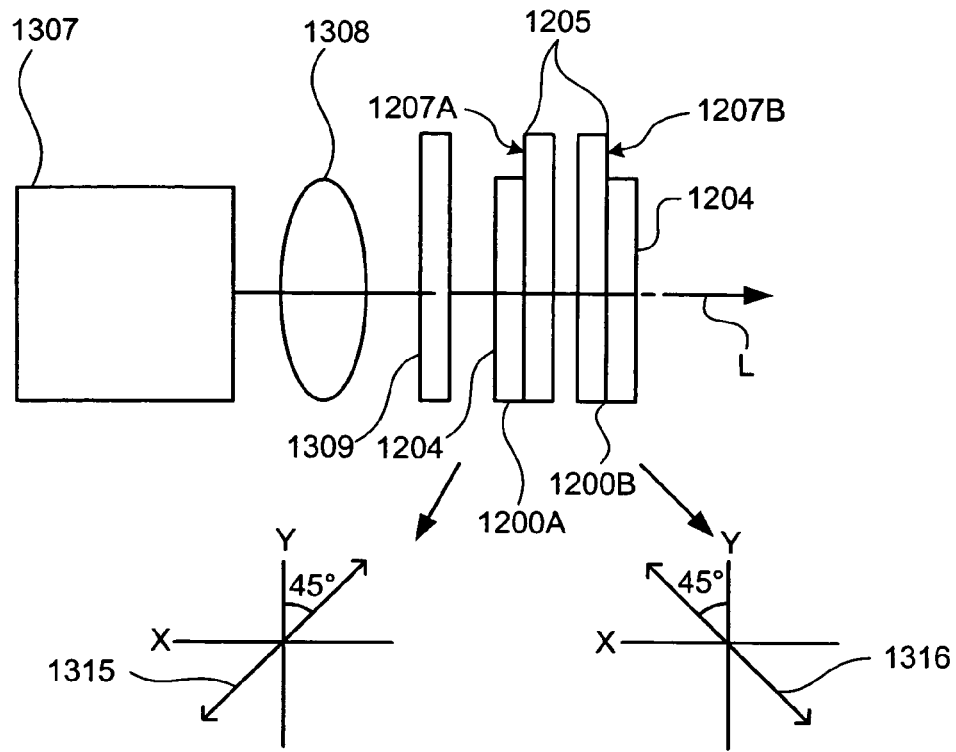
FIG. 13 is an explanatory diagram of an arrangement of a light source and a liquid crystal element unit in the optical rotation angle measuring apparatus that includes the two liquid crystal elements.

FIG. 13 is an explanatory diagram of an arrangement of a light source and a liquid crystal element unit in the optical rotation angle measuring apparatus that includes two liquid crystal elements 1200 (1200A and 1200B). A light source 1307 is a light emitting source such as a diode. A lens 1308 is a lens for collimating a light from the light source 1307 into a parallel light. A polarizer 1309 is an optical element for transmitting a light only in a vertical direction.

The first liquid crystal element 1200A has the structure shown in FIG. 12, in which structure an electrode cut-out surface 1207A is arranged on an incident light side. The second liquid crystal element 1200B has the structure shown in FIG. 12, in which an electrode cut-out surface 1207B is arranged on an emission light side.

Namely, if the counter substrate 1204 of the second liquid crystal element 1200B is arranged to be adjacent to the electrode substrate 1205 of the first liquid crystal element 1200A, it is difficult to lead out a wiring to the second liquid crystal element 1200B. This is because the electrode substrate 1205 of the first liquid crystal element 1200A is an obstacle to the wiring. As shown in FIG. 13, by contrast, if the electrode substrate 1205 of the second liquid crystal element 1200B is arranged to be adjacent to the electrode substrate 1205 of the first liquid crystal element 1200A, no obstacle is present. It is, therefore, possible to easily lead out the wiring from electrode cut-out surfaces 1207A and 1207B. In FIG. 13, the optical path L is a route of a light and an emission direction of the light is indicated by an arrow.

An orientation direction 1315 indicates a liquid crystal parallel orientation direction 1206 of the first liquid crystal element 1200A, relative to an incident light side. The orientation direction 1315 is inclined at 45 degrees counterclockwise with respect to the Y axis. Namely, the liquid crystal parallel orientation direction 1315 of the first liquid crystal element 1200A is orthogonal to a liquid crystal parallel orientation direction 1316 of the second liquid crystal element 1200B relative to the incident light. That is, the optical rotation angle can be stably measured against disturbances such as a temperature change.

According to this fourth embodiment, the liquid crystal elements manufactured at the same steps and equal in liquid crystal parallel orientation direction and structure are arranged back to back, the optical rotation angle can be advantageously stably measured against disturbances such as a temperature change. In addition, a space saving structure by which the apparatus is easy to mount can be advantageously provided.

Fifth Embodiment

Figure 14:
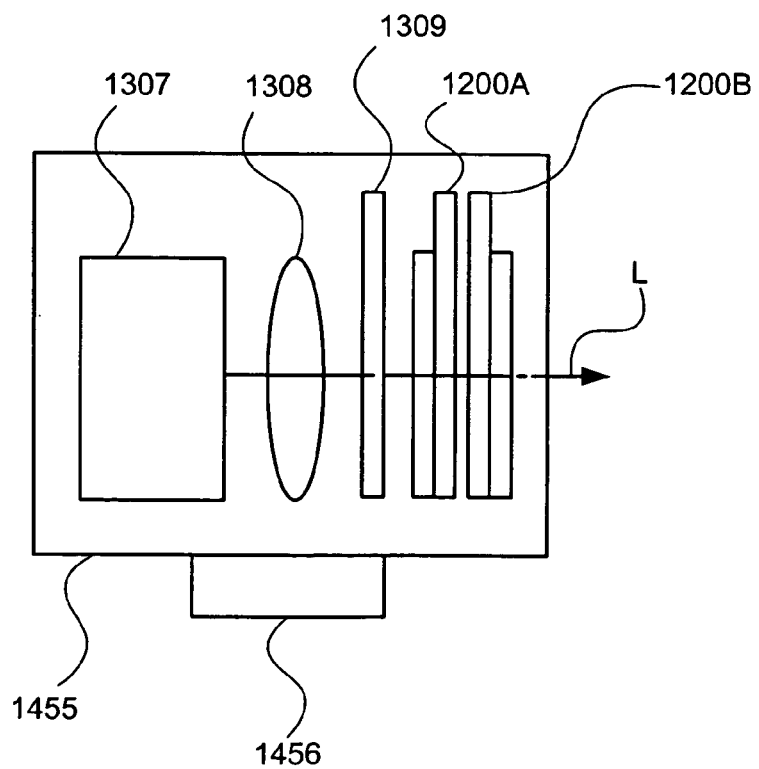
FIG. 14 is a schematic diagram of a case that the arrangement explained in the fourth embodiment is contained in a thermal transmittable holding structure including a temperature controller.

A holding structure in consideration of temperature control over both the liquid crystal elements and the light source unit will be explained. FIG. 14 is a schematic diagram of a case that the arrangement explained in the fourth embodiment is contained in a thermal transmittable holding structure including a temperature controller. Like constituent elements as those shown in FIG. 13 are denoted by like reference symbols and will not be explained herein.

A housing 1455 is a thermal transmittable holding mechanism that holds the lens 1308, the polarizer 1309, the first liquid crystal element 1200A, and the second liquid crystal element 1200B. A thermal converter element 1456 is an element such as a Peltier element for temperature control. Namely, by allowing the thermal converter element 1456 to control a temperature of the housing 1455, temperatures of both the light source and the liquid crystal elements 1200 are controlled.

Figure 15:
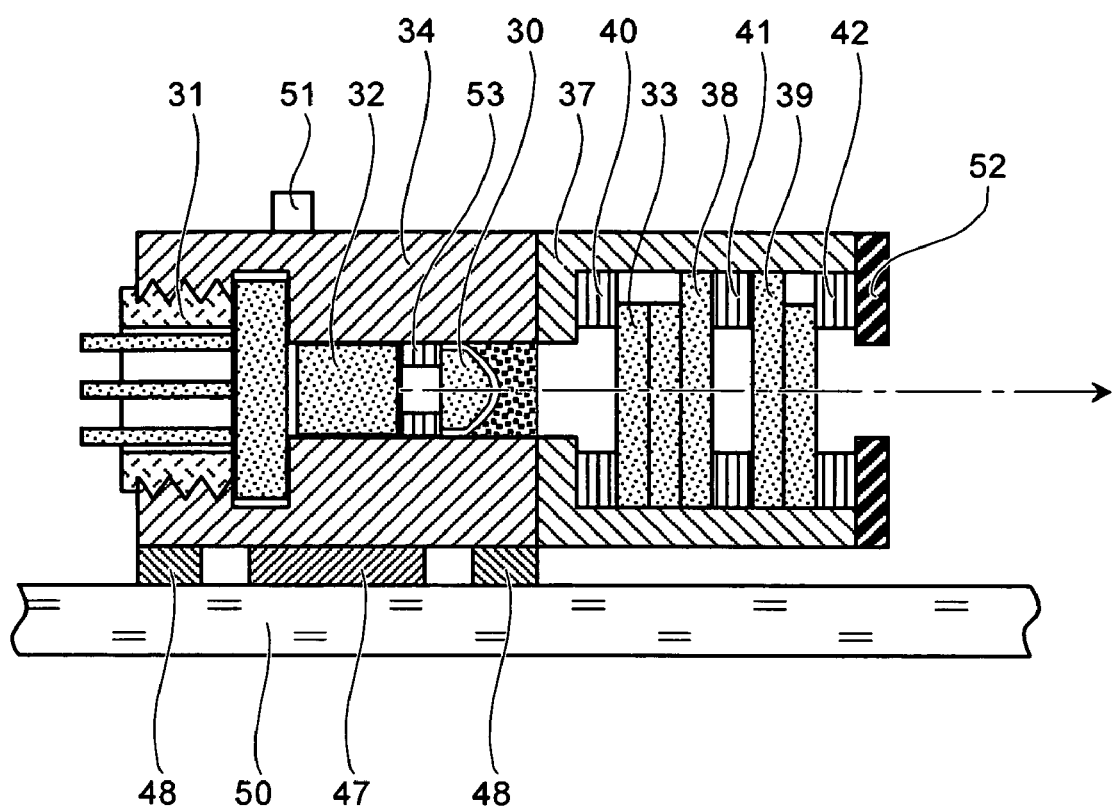
FIG. 15 is a sectional view of a specific optical rotation angle measuring apparatus.

FIG. 15 is a sectional view of a specific optical rotation angle measuring apparatus. A laser diode 32 corresponds to the light source 1307 show in FIG. 14. A collimator lens 30 corresponds to the lens 1308 shown in FIG. 14. A polarizer 33 corresponds to the polarizer 1309 shown in FIG. 14. A liquid crystal element 38 corresponds to the first liquid crystal element 1200A shown in FIG. 14. A liquid crystal element 39 corresponds to the second liquid crystal element 1200B shown in FIG. 14. The polarizer 33 is bonded to the liquid crystal element 38.

An LD holder 34, which is made of aluminum, is a unit that holds the laser diode 32 and the collimator lens 30. An LD stopper 31 is a component that fixes the laser diode 32 to the LD holder 34. After installing the laser diode 32 in the LD holder 34, the laser diode 32 is forcibly filled in the LD holder 34, thereby fixing the laser diode 32 into the LD holder 34. A thermistor 51, which is a temperature measuring element, measures a temperature of the LD holder 34.

A liquid crystal element holder 37, which is made of aluminum, is a unit that holds the polarizer 33 and the liquid crystal elements 38 and 39. A spacer 40 is a buffer between the liquid crystal element 38, to which the polarizer 33 is bonded, and the liquid crystal element holder 37. A spacer 42 is a buffer between the liquid crystal elements 38 and 39 and made of rubber that is a soft material. A liquid crystal stopper 52 is a component for fixedly screwing the two liquid crystal elements 38 and 39 into the liquid crystal element holder 37 using a screw (not shown).

The LD holder 34 is connected to the liquid crystal element holder 37. Since both holders are aluminum holders, they transmit heat. A heat insulating spacer 48 is a plastic material provided to thermally insulate a substrate 50, the LD holder 34, and the liquid crystal element holder 37. A Peltier element 47, which is provided between the LD holder 34 and the substrate 50, performs a heat exchange with an outside through the substrate according to a temperature measuring result of the thermistor 51 so as to keep the temperature of the LD holder 34 to be equal to a predetermined temperature.

With the structure of the optical measuring apparatus according to this fifth embodiment, the temperature of the LD holder 34 is kept constant, and that of the liquid crystal element holder 37 is also kept constant by the thermal transmittable characteristic. Furthermore, as explained in the fourth embodiment, the two liquid crystal elements are arranged back to back, whereby the liquid crystal orientation directions of the elements are orthogonal to each other. It is, therefore, advantageously possible to accurately and stably measure the optical rotation angle and facilitate wirings for input.

The fourth and the fifth embodiments have been explained above. However, for simultaneously controlling temperatures of the light source and the liquid crystal elements, the number of liquid crystal elements is not limited to a specific number and the temperature control can be realized whether the number of liquid crystal elements is one or two or more. In addition, the case that the LD holder 34 and the liquid crystal element holder 37 are separately provided has been explained. Needless to say, the LD holder 34 and the liquid crystal element holder 37 can be integrated into one holder if the temperature control is exercised for one system. In addition, the holders can be divided into smaller regions.

The case that the LD holder 34 includes the laser diode 32 and the collimator lens 30 and the liquid crystal element holder 37 includes the liquid crystal elements 38 and 39 and the polarizer 33 has been explained. However, it suffices that the LD holder 34 and the liquid crystal element holder 37 include the light source and the liquid crystal elements, respectively.

Furthermore, while the case that the liquid crystal elements 38 and 39 are arranged so that electrode substrates are arranged back to back has been explained, it is obvious that the liquid crystal orientation directions of the two liquid crystal elements are made orthogonal to each other by arranging the counter substrates thereof back to back. In this case, a space generated by thicknesses of the two counter substrates arranged back to back can advantageously facilitate leading out wirings.

Sixth Embodiment

Figure 16:
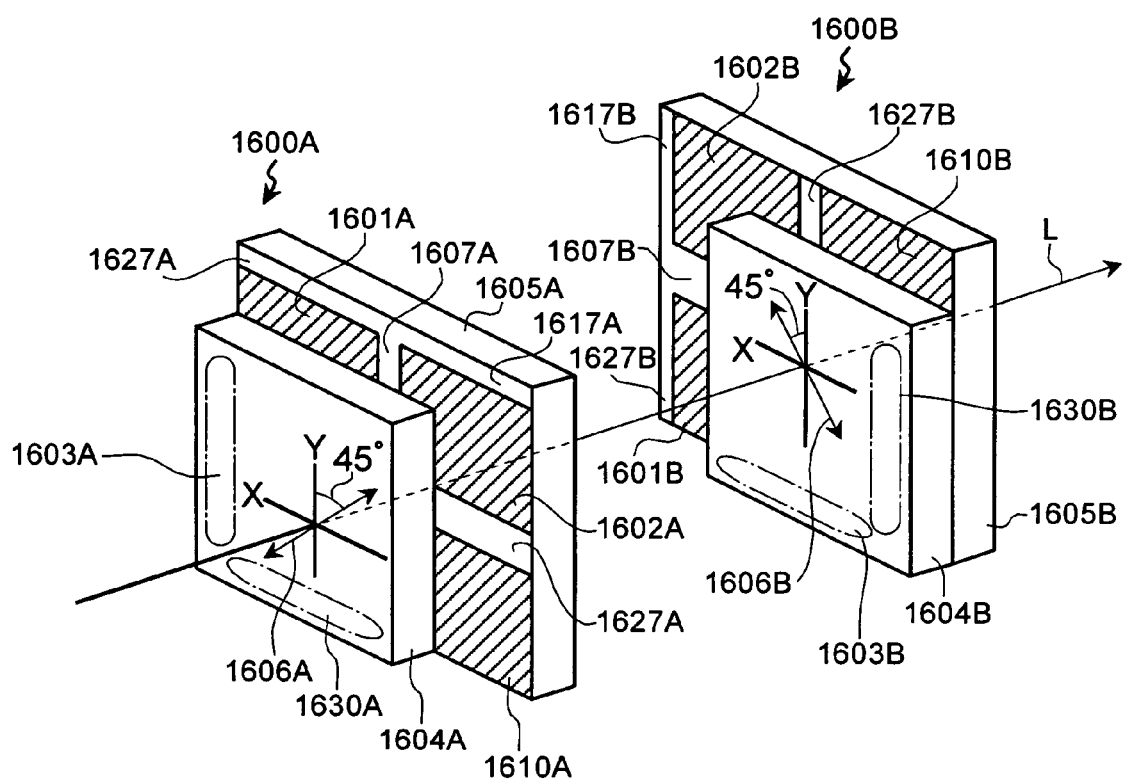
FIG. 16 is an explanatory diagram of an arrangement configuration of two liquid crystal elements different in structure from the two liquid crystal elements shown in FIG. 12.

Liquid crystal elements different in structure to the liquid crystal element shown in FIG. 12 will be explained. FIG. 16 is an explanatory diagram of an arrangement configuration of liquid crystal elements 1600A and 1600B different in structure from the liquid crystal elements 1200A and 1200B shown in FIG. 12. In FIG. 16, the liquid crystal elements 1600A and 1600B are arranged in series on the optical path L. This optical path L is the route of the light from the light source to the photodiode.

The liquid crystal element 1600A is configured to hold a liquid crystal between a counter substrate 1604A and an electrode substrate 1605A. By applying a voltage to an electrode (not shown) formed on the counter substrate 1604A and an electrode (not shown) formed on the electrode substrate 1605A, a state of the liquid crystal is changed to thereby change a state of a light passing through the liquid crystal element 1600A.

The counter substrate 1604A and the electrode substrate 1605A are equally rectangular substrates but different in magnitude. Specifically, the electrode substrate 1605A is larger than the counter substrate 1604A. By holding the liquid crystal between the counter substrate 1604A and the electrode substrate 1605A so that an angle of the counter substrate 1604A coincides with a corresponding angle of the electrode substrate 1605A, an L-shaped electrode cut-out region 1607A is formed.

An electrode substrate input electrode 1602A is formed into a generally L-shaped electrode in a bent region 1617A of the L-shaped electrode cut-out region 1607A. The electrode substrate input electrode 1602A is electrically connected to the electrode formed on the electrode substrate 1605A.

Counter substrate input electrodes 1601A and 1610A are formed on both ends 1627 of the L-shaped electrode cut-out region 1607A, respectively. The respective counter substrate input electrodes 1601A and 1610A are electrically connected to the electrode formed on the counter substrate 1604A from electrode transfer regions 1603A and 1630A through conductive particles, respectively.

It is assumed herein that on a plane orthogonal to the optical path L that represents an incident direction, an axis that represents a horizontal direction is the X axis and an axis orthogonal to the X axis is the Y axis. An orientation direction 1606A indicates that the liquid crystal is oriented in parallel to a direction at 45 degrees clockwise with respect to the Y axis.

Namely, in the liquid crystal element 1600A shown in FIG. 16, the counter substrate input electrode 1601A and the electrode substrate input electrode 1602A are arranged in series along one end side of the electrode substrate 1605A on a surface of the electrode substrate 1605A near the one end side. In addition, the counter substrate input electrode 1610A and the electrode substrate input electrode 1602A are arranged in series along one end side orthogonal to the former end side on the surface of the electrode substrate 1605A near the one end side.

The liquid crystal element 1600B is equal in configuration to the liquid crystal element 1600A, and obtained by rotating counterclockwise the liquid crystal element 1600A by 90 degrees. Accordingly, constituent elements 1601B to 1607B, 1610B, 1617B, 1627B, and 1630B of the liquid crystal element 1600B are equal in configuration to the constituent elements 1601A to 1607A, 1610A, 1617A, 1627A, and 1630A of the liquid crystal element 1600A, respectively.

The liquid crystal element 1600B is arranged so that the counter substrate 1604B faces the electrode substrate 1605A of the liquid crystal element 1600A. The counter substrate input electrode 1601A and electrode substrate input electrode 1602A of the liquid crystal element 1600A are equal in lead-out direction (the Y-axis direction in FIG. 16) to the counter substrate input electrode 1610B and an electrode substrate input electrode 1602B of the liquid crystal element 1600A, respectively.

It is thereby possible to connect wirings of the liquid crystal elements 1600A and 1600B from the same lead-out direction (the Y-axis direction in FIG. 16). A space of the wirings of the liquid crystal elements 1600A and 1600B can be, therefore, saved, and the optical rotation angle measuring apparatus can be made small in size.

Figure 17:
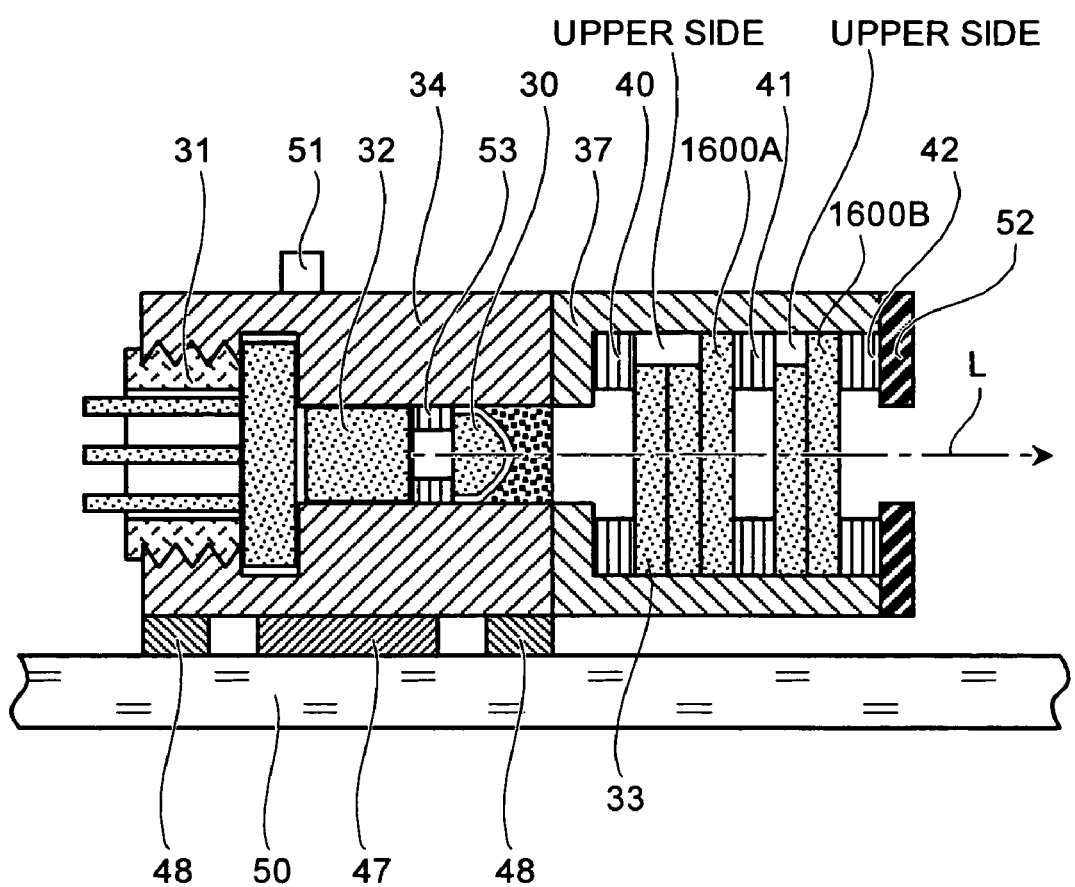
FIG. 17 is a sectional view of an optical rotation angle measuring apparatus that employs the two liquid crystal elements shown in FIG. 16.
Figure 18:
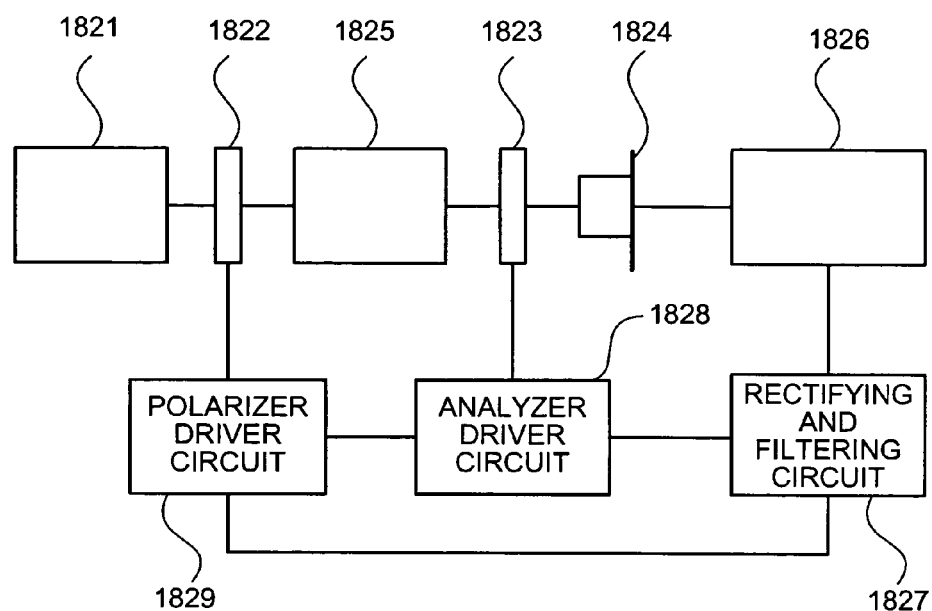
FIG. 18 is an explanatory diagram of a conventional optical rotation angle measuring apparatus using the method for vibrating the polarization plane.
Figure 19:
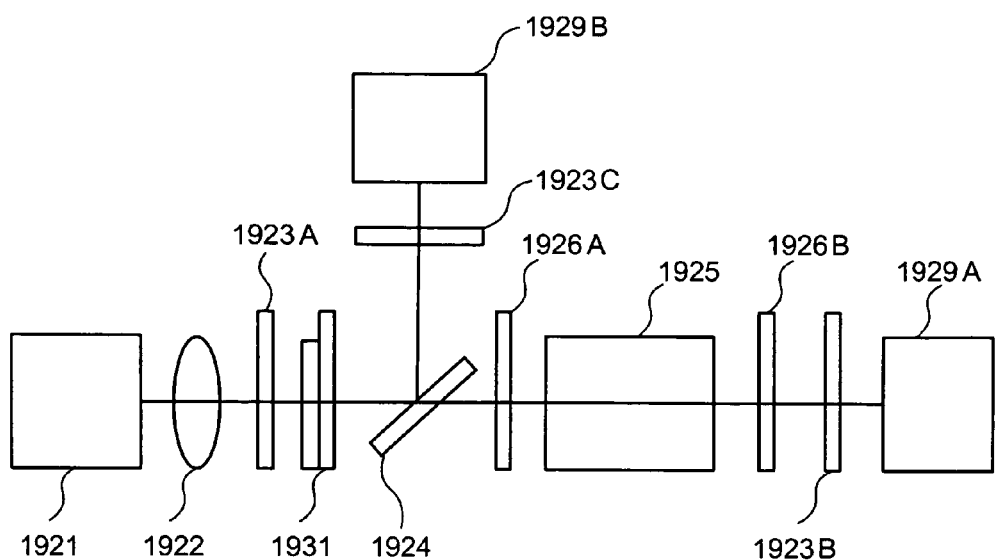
FIG. 19 is an explanatory diagram of an optical system of a conventional concentration measuring apparatus.

FIG. 17 is a sectional view of the optical rotation angle measuring apparatus in which the liquid crystal elements 1600A and 1600B shown in FIG. 16 are employed. In FIG. 17, like constituent elements as those shown in FIG. 15 are denoted by like reference symbols and will not be explained herein.

The liquid crystal element holder 37, which is made of aluminum, is a unit that holds the polarizer 33 and the liquid crystal elements 1600A and 1600B. The spacer 40 is a buffer between the liquid crystal element 1600A, to which the polarizer 33 is bonded, and the liquid crystal element holder 37. The spacer 42 is a buffer between the liquid crystal elements 1600A and 1600B and made of rubber that is a soft material. The liquid crystal stopper 52 is a component for fixedly screwing the two liquid crystal elements 1600A and 1600B into the liquid crystal element holder 37 using a screw (not shown).

With the structure of this optical measuring apparatus, even if one of the liquid crystal elements 1600A and 1600B equal in structure is rotated by 90 degrees so that the orientation directions thereof are orthogonal to each other, the counter substrate input electrode 1601A and the electrode substrate input electrode 1602A formed on the liquid crystal element 1600A are located in the same direction (upward direction in FIGS. 16 and 17) as the counter substrate input electrode 1601B and the electrode substrate input electrode 1602A formed on the liquid crystal element 1600B.

It is, therefore, possible to share a wiring space between the counter substrate input electrode 1601A and the electrode substrate input electrode 1602A formed on the liquid crystal element 1600A and the counter substrate input electrode 1601B and the electrode substrate input electrode 1602B formed on the liquid crystal element 1600B. This can facilitate leading out wirings. In addition, a space within the optical rotation angle measuring apparatus can be saved and the optical rotation angle measuring apparatus can be made small in size.

As explained so far, the optical rotation angle measuring apparatus according to one of the fourth to the sixth embodiments is the optical measuring apparatus for holding the first liquid crystal element and the second liquid crystal element each having the liquid crystal provided between the electrode substrate and the counter substrate. The first liquid crystal element and the second liquid crystal element have input electrodes formed on the electrode substrates, respectively, and the counter substrates of the first and the second liquid crystal elements are arranged back to back.

Furthermore, the optical rotation angle measuring apparatus according to one of the fourth to the sixth embodiments is the optical measuring apparatus for holding the first liquid crystal element and the second liquid crystal element each having the liquid crystal provided between the electrode substrate and the counter substrate. The first liquid crystal element and the second liquid crystal element have input electrodes formed on the electrode substrates, respectively, and the electrode substrates of the first and the second liquid crystal elements are arranged back to back.

Furthermore, the optical rotation angle measuring apparatus according to one of the fourth to the sixth embodiments is the optical measuring apparatus for holding the light source and the liquid crystal elements. The light source holding unit that holds the light source and the liquid crystal element holding unit that holds the liquid crystal elements transmit heat to each other. It is preferable that the light source holding unit or the liquid crystal element holding unit includes the heat exchange element for temperature control. It is also preferable that the light source holding unit or the liquid crystal element holding unit includes the heat exchange element for temperature control.

While the invention of the optical rotation angle measuring apparatus using the liquid crystal elements has been made thus far, the structure of holding the optical elements and the liquid crystal elements is important for improving the measuring accuracy and making the apparatus small in size. In each of the optical rotation angle measuring apparatus according to the fourth and the fifth embodiments, the two liquid crystal elements the liquid crystal orientation directions of which are orthogonal to each other are provided back to back if the elements are arranged in series relative to the incident light particularly for purposes of improving the measuring accuracy and the stability.

The first liquid crystal element and the second liquid crystal elements are liquid crystal elements manufactured at the same steps and equal in the orientation direction. Namely, by arranging the two liquid crystal elements back to back, the liquid crystal orientation directions of the two elements are orthogonal to each other.

Furthermore, by arranging the counter substrates of the two liquid crystal elements to face each other, that is, arranging the counter substrates back to back, the wirings to the counter substrate input electrode and the electrode substrate input electrode formed on each electrode substrate can be easily provided.

Furthermore, if the optical rotation angle is measured with high accuracy, it is necessary to control the temperature of the liquid crystal element using the heat exchange element such as the Peltier element. In addition, it is necessary to control the temperature of the laser diode (LD) that serves as the light source so as to suppress heat generation and suppress delicate wavelength fluctuations. To do so, the liquid crystal holding unit and the LD holding unit are formed integrally or the housing that transmits heat is connected to the units, the optical rotation angle can be measured stably with high accuracy with the temperatures of both the light source and the liquid crystal elements controlled.

As explained so far, according to the present invention, by using the small-sized liquid crystal element that can be driven at low power consumption, the optical rotation angle by the sample can be advantageously, accurately measured.

The delicate modulation width can be advantageously changed using the driving voltage range in which the modulation characteristic of the liquid crystal element is stable. In addition, the optical rotation angle by the sample can be advantageously, accurately measured.

The requirements of the modulation range of the liquid crystal element and the absolute value of the modulation amount can be advantageously relaxed. It is thereby advantageously possible to facilitate designing the liquid crystal element and relax the manufacturing accuracy.

Furthermore, it is advantageously possible to cancel the fluctuations in the liquid crystal element due to the external environment, stabilize the measurement result, and improve the measuring accuracy.

By employing the liquid crystal elements equal in the orientation direction as the first and the second liquid crystal elements, and arranging the first and the second liquid crystal elements back to back, the liquid crystal orientation directions of the two elements are orthogonal to each other. The influence of the disturbances caused by a temperature change or the like can be, therefore, advantageously reduced.

The counter substrate input electrode and the electrode substrate input electrode between which the liquid crystal is held are formed on the electrode substrate. Therefore, by arranging the counter substrate of the two liquid crystal elements back to back, it is advantageously possible to widen the space of the wirings to the electrodes and facilitate providing the wirings.

In addition, the liquid crystal element holding unit and the light source holding unit are formed integrally with each other to provide the housing that transmits heat. It is thereby advantageously possible to control the temperatures of the liquid crystal elements and the light source using one heat exchange element.

INDUSTRIAL APPLICABILITY

As explained so far, the present invention is suited to provide the optical rotation angle measuring apparatus for measuring the concentration of a scatterer including a living body, a matter derived from the living body such as urine or sweat, an optically active material contained in a sample such as fruits juice or chemicals, for example, a saccharide, an amino acid, a protein, or a vitamin, in a no-contact fashion.

The invention claimed is:

1. An optical rotation angle measuring apparatus comprising:
    a linearly polarized light output section that outputs a linearly polarized light;
    a phase modulation section that is configured so that fluctuations in modulation characteristic of a first phase modulation unit having a first polarization axis in a predetermined direction and a second phase modulation unit having a second polarization axis orthogonal to the first polarization axis cancel each other, and that modulates a phase of the linearly polarized light output from the linearly polarized light output section;
    a signal supply section that supplies a modulation signal having a predetermined amplitude for modulating the phase of the linearly polarized light to one of the first and the second phase modulation units;
    a light intensity detection section that detects an intensity of a light that is emitted from the phase modulation section and transmitted by a sample containing an optically active material that rotates a polarization plane of the light, following a supply of the modulation signal to one of the first and the second phase modulation units by the signal supply section; and
    an optical rotation angle calculation section that calculates an optical rotation angle by the sample based on the modulation signal supplied from the signal supply section and the intensity of the light detected by the light intensity detection section.

2. The optical rotation angle measuring apparatus according to claim 1, wherein the signal supply section further supplies a preset offset signal to the first and the second phase modulation units, and the light intensity detection section further detects the intensity of the light that is emitted from the phase modulation section and transmitted by the sample containing the optically active material that rotates the polarization plane of the light, following a supply of the predetermined offset signal to the first and the second phase modulation units by the signal supply section.

3. The optical rotation angle measuring apparatus according to claim 2, wherein the first phase modulation unit includes a first liquid crystal element a liquid crystal orientation direction of which is a direction of the first polarization axis, and the second phase modulation unit includes a second liquid crystal element which is different from the first liquid crystal element and a liquid crystal orientation direction of which is a direction of the second polarization axis.

4. The optical rotation angle measuring apparatus according to claim 3, wherein the first and the second liquid crystal elements are liquid crystal elements manufactured at predetermined manufacturing steps, manufactured on an equal liquid crystal substrate, and equal in structure.

5. The optical rotation angle measuring apparatus according to claim 4, wherein the first liquid crystal element is a liquid crystal element manufactured in an arbitrary position on the liquid crystal substrate, and the second liquid crystal element is a liquid crystal element manufactured near the first liquid crystal element on the liquid crystal substrate.

6. The optical rotation angle measuring apparatus according to claim 3, wherein the first and the second liquid crystal elements are homogeneous alignment-type liquid crystal elements.

7. The optical rotation angle measuring apparatus according to claim 3, wherein the first and the second liquid crystal elements include electrode substrates and counter substrates between which liquid crystals are held, respectively, and are equal in the liquid crystal orientation direction and equal in structure, and the first and the second liquid crystal elements are arranged in series to an optical path from the linearly polarized light output section to the light intensity detection section so that the liquid crystal orientation direction of the first liquid crystal element is orthogonal to the liquid crystal orientation direction of the second liquid crystal element.

8. The optical rotation angle measuring apparatus according to claim 7, wherein the first and the second liquid crystal elements are arranged so that the electrode substrates or the counter substrates of the respective liquid crystal elements face each other.

9. The optical rotation angle measuring apparatus according to claim 3, wherein at least one of the first and the second liquid crystal elements includes:

a rectangular first substrate including a first electrode;

a rectangular second substrate including a second electrode, the liquid crystal held between the first electrode and the second electrode;

a first input electrode for inputting the signal from the signal supply section to the first electrode; and a second input electrode for inputting the signal from the signal supply section to the second electrode, wherein the first and the second input electrodes are provided near one end side of the second substrate along the end side, and the first and the second input electrodes are also provided near an end side other than the one end side of the second substrate.

10. The optical rotation angle measuring apparatus according to claim 3, wherein the first liquid crystal element includes:

a rectangular first substrate including a first electrode;

a rectangular second substrate including a second electrode, the liquid crystal being held between the first electrode and the second electrode, the second substrate being larger than the first substrate;

a first input electrode for inputting the signal from the signal supply section to the first electrode; and a second input electrode for inputting the signal from the signal supply section to the second electrode, the first and the second input electrodes are arranged in series near one end side of the second substrate along the end side, and the first and the second input electrodes are arranged in series near an end side orthogonal to the one end side of the second substrate, the second liquid crystal is equal to the first liquid crystal in the liquid crystal orientation direction and in structure, and the first and the second liquid crystal elements are arranged in series on an optical path from the linearly polarized light output section to the light intensity detection section so that the liquid crystal orientation direction of the first liquid crystal element is orthogonal to the liquid crystal orientation direction of the second liquid crystal element.

11. The optical rotation angle measuring apparatus according to claim 3, further comprising:

a liquid crystal element holding section that holds the first and the second liquid crystal elements.

12. The optical rotation angle measuring apparatus according to claim 1 or 2, further comprising:

a pair of quarter-wave plates arranged in series on an optical path from the linearly polarized light output section to the light intensity detection section while the sample is held between the pair of quarter-wave plates.

13. The optical rotation angle measuring apparatus according to claim 2, wherein the first phase modulation unit is a first pixel group constituted by a part of a plurality of pixels that constitute a single liquid crystal element, and the second phase modulation unit is a second pixel group constituted by pixels other than the part of the plurality of pixels that constitute the single liquid crystal element, the other pixels and the part of pixels being alternately arranged.

14. The optical rotation angle measuring apparatus according to claim 13, further comprising:

a condensing section, provided between the first and the second pixel groups and the light intensity detection section, for condensing the light emitted from the first and the second pixel groups and transmitted by the sample containing the optically active material that rotates the polarization plane of the light, and for emitting the light to the light intensity detection section.

15. The optical rotation angle measuring apparatus according to claim 3, wherein the offset signal supplied from the signal supply section is a signal in a section in which a phase modulation amount of the liquid crystal element is linearly changed.

16. The optical rotation angle measuring apparatus according to claim 2, wherein the first phase modulation unit includes a first liquid crystal element a liquid crystal orientation direction of which is a direction of the first polarization axis, the second phase modulation unit includes a second liquid crystal element which is different from the first liquid crystal element and a liquid crystal orientation direction of which is a direction of the second polarization axis, and the offset signal supplied from the signal supply section is a signal in a section in which a phase modulation amount of the liquid crystal element is linearly changed.

17. The optical rotation angle measuring apparatus according to claim 13, wherein the offset signal supplied from the signal supply section is a signal in a section in which a phase modulation amount of the liquid crystal element is linearly changed.

18. The optical rotation angle measuring apparatus according to claim 14, wherein the offset signal supplied from the signal supply section is a signal in a section in which a phase modulation amount of the liquid crystal element is linearly changed.

19. The optical rotation angle measuring apparatus according to claim 4, wherein the first and the second liquid crystal elements are homogeneous alignment-type liquid crystal elements.

20. The optical rotation angle measuring apparatus according to claim 5, wherein the first and the second liquid crystal elements are homogeneous alignment-type liquid crystal elements.

* * * * *